(12) United States Patent
Norton et al.

(10) Patent No.: US 12,337,025 B2
(45) Date of Patent: Jun. 24, 2025

(54) MUTATED E. COLI ENTEROTOXINS AS ANTI-INFLAMMATORY AGENTS

(71) Applicant: Administrators of the Tulane Educational Fund, New Orleans, LA (US)

(72) Inventors: Elizabeth Bray Norton, New Orleans, LA (US); John David Clements, Dadeville, AL (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 185 days.

(21) Appl. No.: 17/053,635

(22) PCT Filed: May 7, 2019

(86) PCT No.: PCT/US2019/031193
§ 371 (c)(1),
(2) Date: Nov. 6, 2020

(87) PCT Pub. No.: WO2019/217473
PCT Pub. Date: Nov. 14, 2019

(65) Prior Publication Data
US 2021/0187064 A1 Jun. 24, 2021

Related U.S. Application Data

(60) Provisional application No. 62/667,992, filed on May 7, 2018.

(51) Int. Cl.
| | |
|---|---|
| *A61K 38/16* | (2006.01) |
| *A61K 47/36* | (2006.01) |
| *A61K 47/69* | (2017.01) |
| *A61P 29/00* | (2006.01) |
| *C07K 14/245* | (2006.01) |
| *C07K 16/28* | (2006.01) |

(52) U.S. Cl.
CPC ............ *A61K 38/164* (2013.01); *A61K 47/36* (2013.01); *A61K 47/6913* (2017.08); *A61P 29/00* (2018.01); *C07K 14/245* (2013.01); *C07K 16/2845* (2013.01)

(58) Field of Classification Search
None
See application file for complete search history.

(56) References Cited

U.S. PATENT DOCUMENTS

| | | | |
|---|---|---|---|
| 6,777,546 B2 * | 8/2004 | Langridge .......... | C12N 15/8216 435/69.3 |
| 7,208,155 B1 * | 4/2007 | Williams ............... | A61K 38/45 424/275.1 |
| 7,560,436 B2 * | 7/2009 | Raz .................... | A61K 31/5377 514/44 R |
| 8,110,197 B2 * | 2/2012 | Hsu ...................... | C07K 14/245 424/234.1 |
| 2003/0113338 A1 | 6/2003 | Pizza | |
| 2003/0113345 A1 | 6/2003 | Clements | |
| 2010/0221349 A1 | 9/2010 | Fuller | |
| 2011/0143994 A1 | 6/2011 | Lycke | |
| 2013/0129756 A1 | 5/2013 | Gorvel | |

FOREIGN PATENT DOCUMENTS

WO WO2013/147232 A1 10/2013

OTHER PUBLICATIONS

Fakhoury et al. Journal of Inflammation Research, 2014; 7:113-120.*
Kelly et al. Journal of Drug Delivery. vol. 22, Article ID 727241, 11 pages, doi:10.1155/2011/727241 2011.*
Baert et al. International Journal of Nanomedicine 2016:11 2463-2469.*
Targan et al.A, J Gastroenterol., 2016, 111(11):1599-1607.*
Hueber et al. Gut, 2012, 61:1693-1700.*
Biopharma Dive Brief. Celgene calls it quits on expensive Crohn's drug. https://biopharmadive.com/news/celgene-crohns-drugs/507797 Oct. 20, 2017.*
Valatas et al. Am J Physiol Gastrointest Liver Physiol 305: G763-G785, 2013.*
Wadman et al. Science Jan. 13, 2023;379(6628):127-128.*
Katsandegwaza et al Int J Mol Sci. Aug. 2022; 23(16):9344.*
Cieplak et al. Journal of Biological Chemistry, vol. 270, Issue 51, Dec. 22, 1995, pp. 30545-35550.*
Park et al. Experimental and Molecular Medicine, vol. 31, No. 2, 101-107, Jun. 1999.*
Norton et al. Infection and Immunity, Jul. 2012, vol. 80 No. 7 p. 2426-p. 2435.*
Jobling et al. Journal of Bacteriology, Jul. 2001, vol. 183, No. 13, p. 4024-4032.*
Lobet et al. Infection and Immunity, Sep. 1991, vol. 59 No. 9, p. 2870-p. 2879.*
Baudier, R., "Research Funding extended for E112K as a Novel Therapy for IBD", Norton Lab website, Jan. 20, 2017, Tulane Med Sch, New Orleans, LA, US. Accessed Sep. 5, 2019.
Baudier, R., "Newly released review of mucosal vaccine adjuvant, dmLT", Norton Lab website, Aug. 10, 2018, Tulane Med Sch, New Orleans, LA, US. Accessed Nov. 4, 2020.
Dehaan, et al., Mutants of the *Escherichia coli* Heat-Labile Enterotoxin with Reduced ADP-Ribosylation Activity or No. Activity . . . = , Infect Imm, 1996, pp. 5413-5416, v.64(12).

(Continued)

*Primary Examiner* — Oluwatosin A Ogunbiyi
(74) *Attorney, Agent, or Firm* — Laurence J. Hyman; Hyman IP Law

(57) ABSTRACT

The invention provides compositions and methods for reducing symptoms of inflammation by administering therapeutically effective amounts of (a) (1) enterotoxic *E. coli* heat labile detoxified toxin A subunit that interferes with the function of ADP-ribosylation factor and inhibits ADP-ribosylation, or (2) A1 subunit that interferes with the function of ADP-ribosylation factor and inhibits ADP-ribosylation, or both (1) and (2), and (b) a carrier that causes internalization of the A subunit or A1 subunit, or both, into cells.

19 Claims, 13 Drawing Sheets

(56) References Cited

OTHER PUBLICATIONS

Lin et al., *Escherichia coli* Heat-Labile Detoxified Enterotoxin Modulates Dendritic Cell Function and Attenuates . . . , PLoS One, 2014, pp. 1-13, v. 9(3).
Clements and Norton, "The Mucosal Vaccine Adjuvant LT (R192G/L211A) or dmLT," mSphere, Jul./Aug. 2018, p. 1-17, v.3(4).
Young, L. International Search Report, PCT/US2019/031193, Oct. 11, 2019.
Young, L. Written Opinion, PCT/US2019/031193, Oct. 11, 2019.
De Haan, L., et al., Mucosal immunogenicity and adjuvant activity of the recombinant A subunit of the *Escherichia coli* heat-labile enterotoxi, Immunol. 1999, p. 706-713, v. 97.

\* cited by examiner

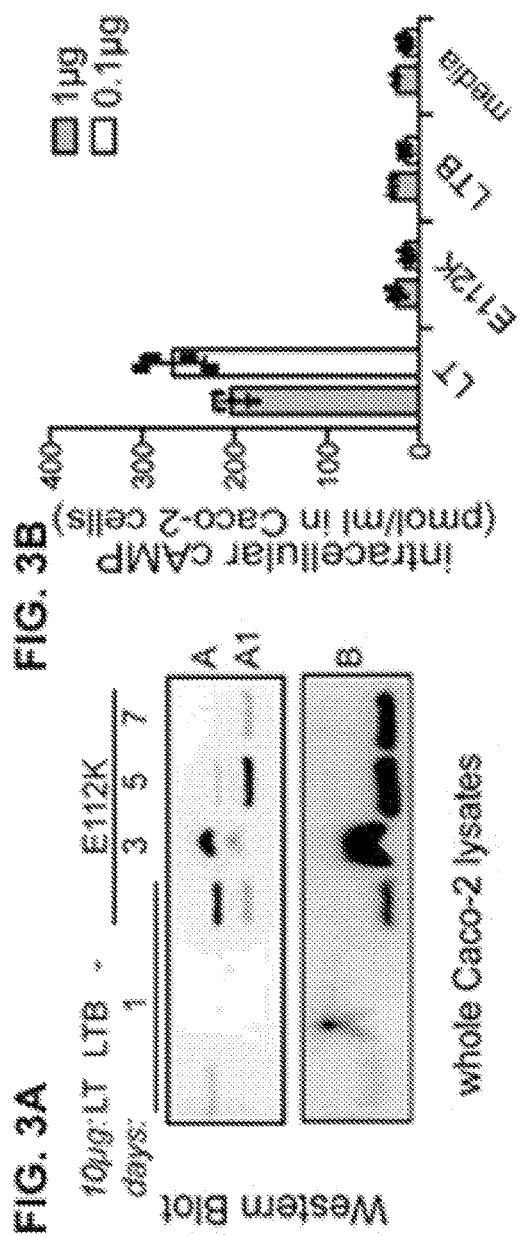
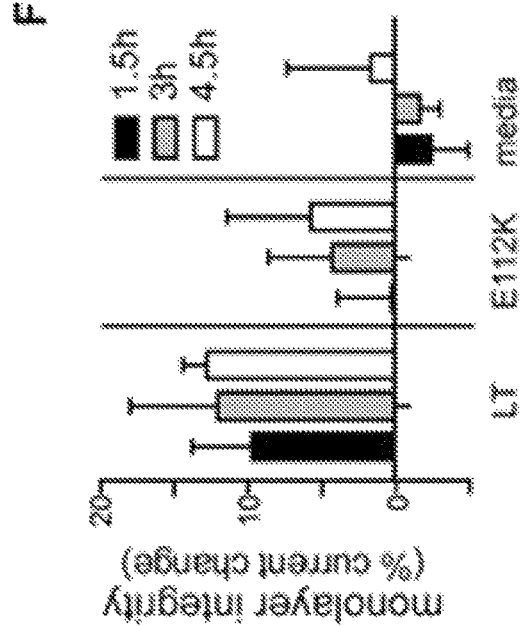
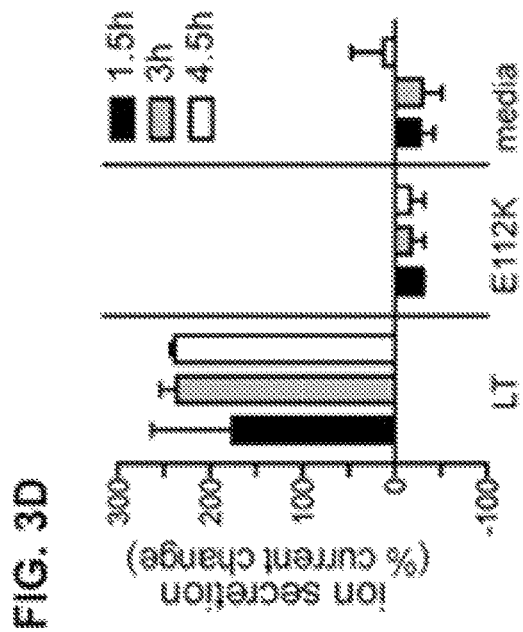

FIG. 6A
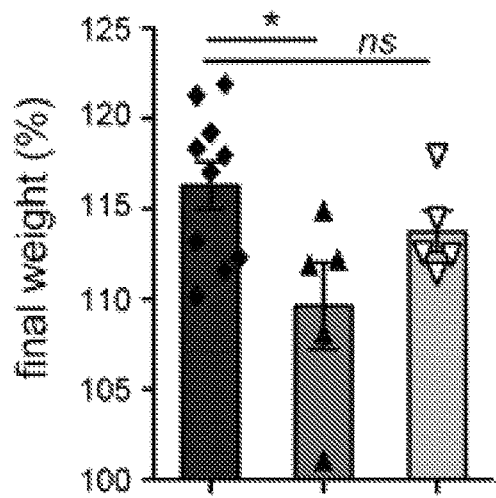
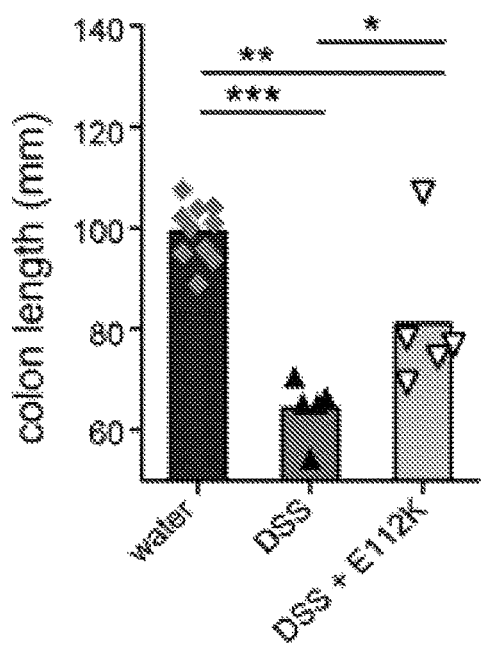
DSS Model
FIG. 6B
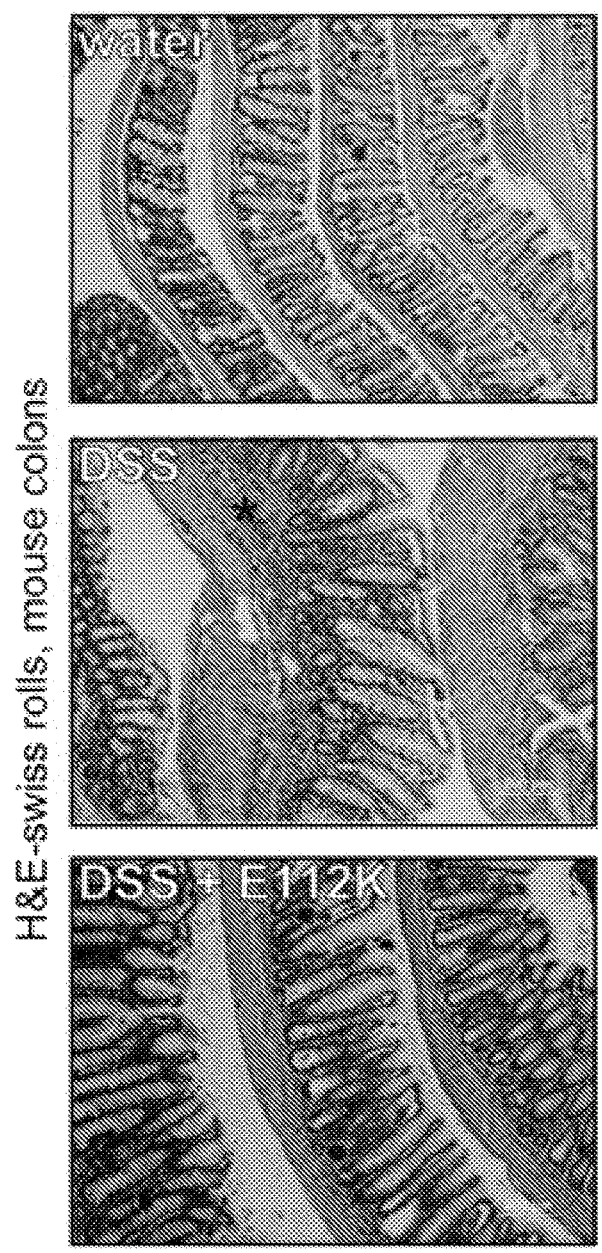

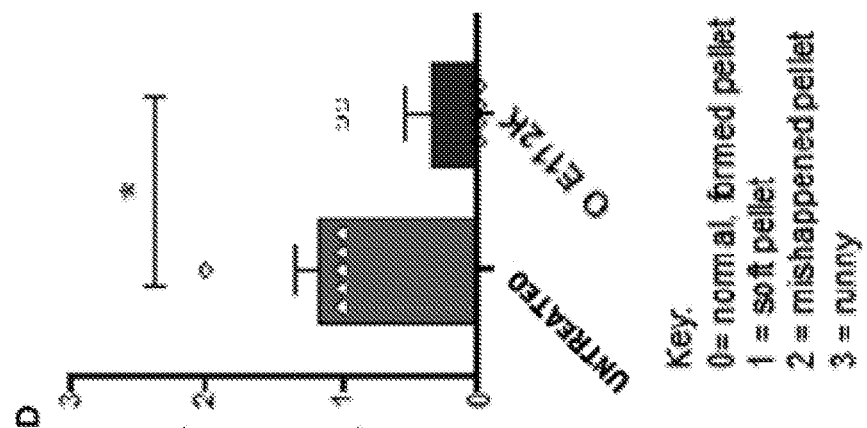
FIG. 8A
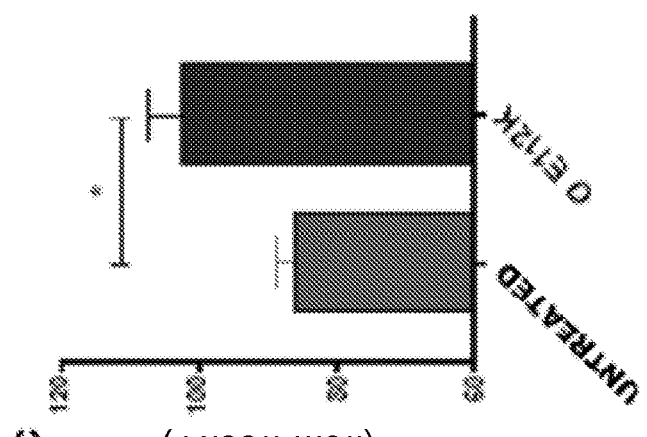
FIG. 8B
FIG. 8C
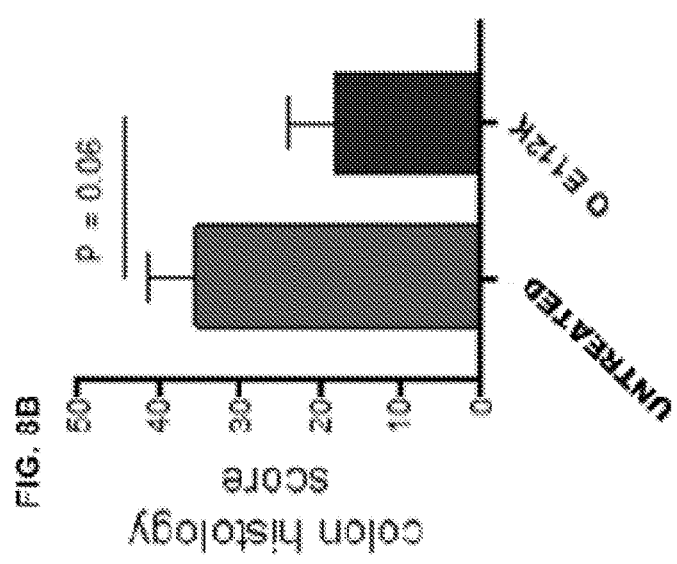
FIG. 8D

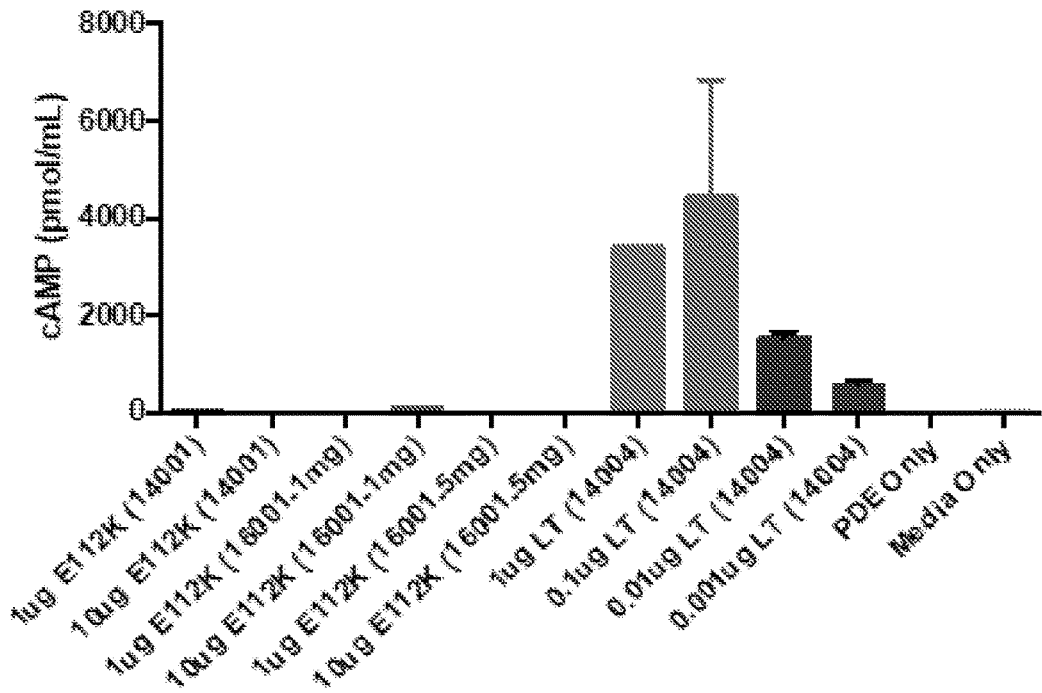
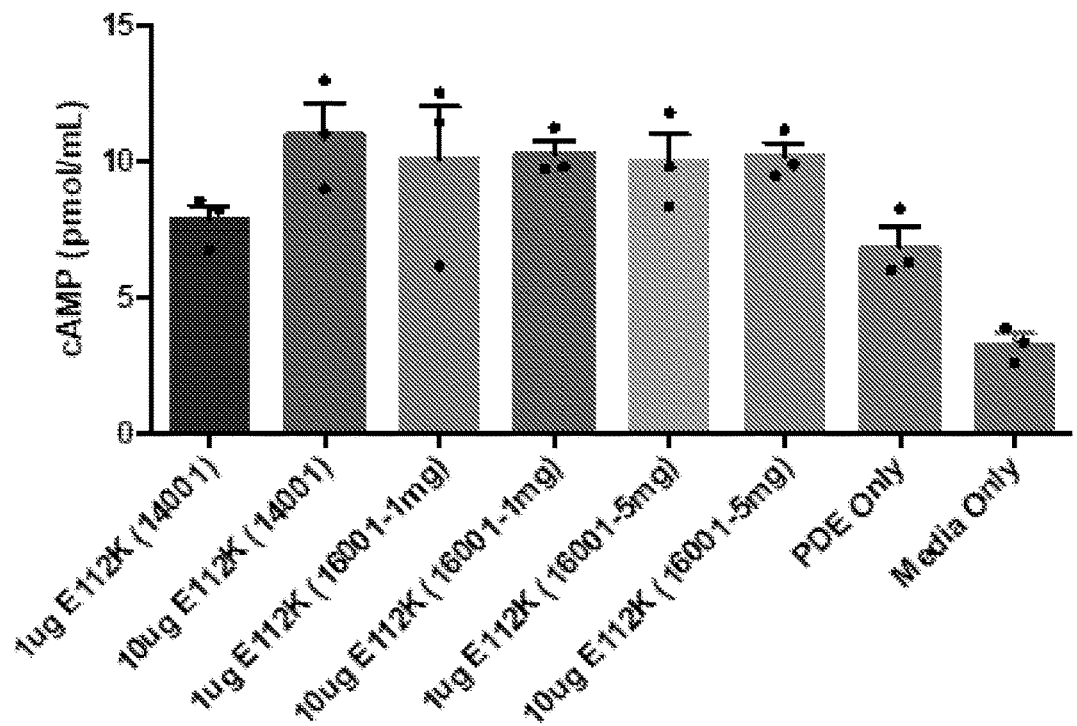
FIG. 10

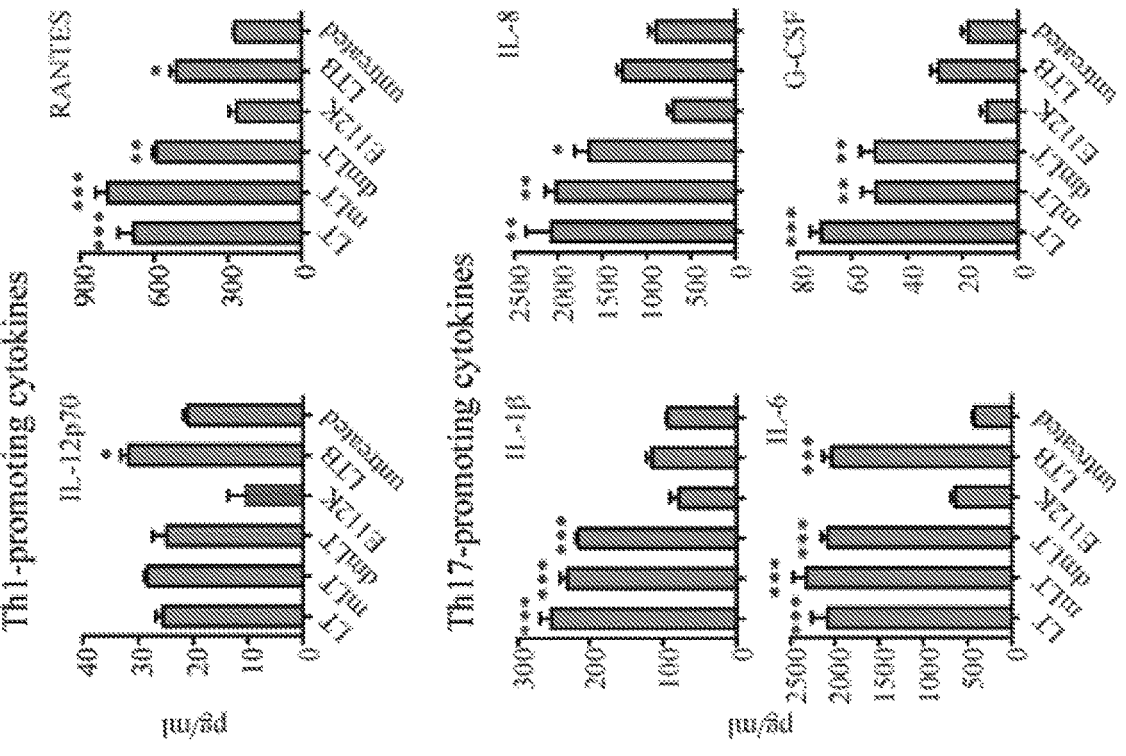
FIG. 13C
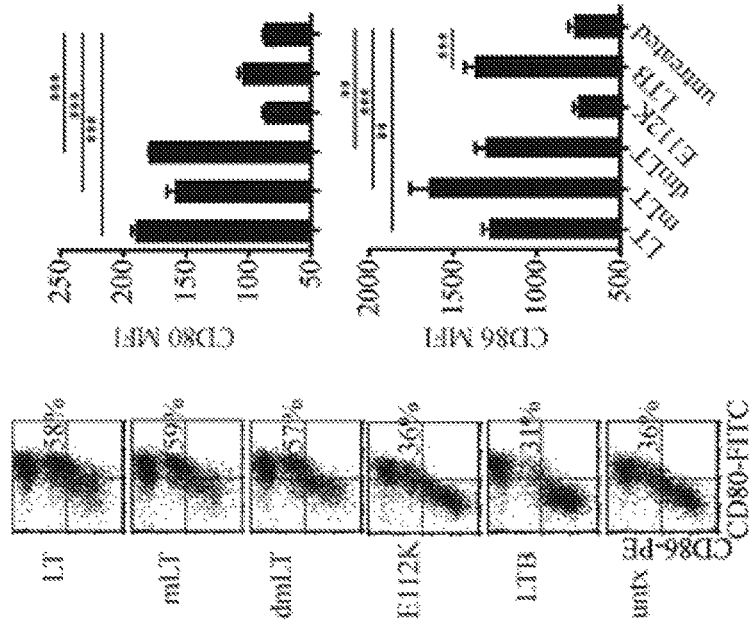
FIG. 13A
FIG. 13B
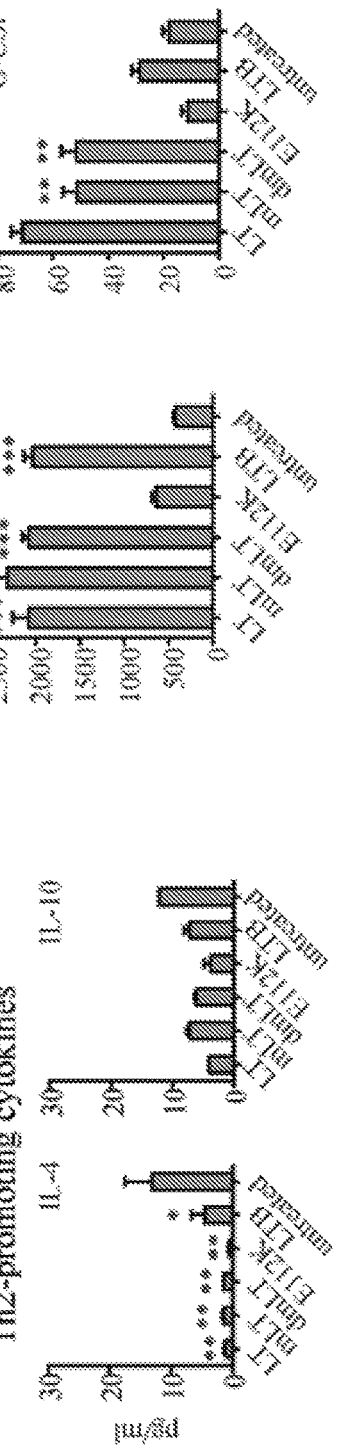

MUTATED E. COLI ENTEROTOXINS AS ANTI-INFLAMMATORY AGENTS

CROSS-REFERENCE TO RELATED APPLICATIONS

This application is a national stage application under 35 U.S.C. § 371 of International Application No. PCT/US19/031193, filed May 7, 2019, which claimed priority to, and the benefit of, U.S. Provisional Patent Application No. 62/667,992, filed May 7, 2018. This application claims priority to, and the benefit of, both of the applications identified above, the contents of which are hereby incorporated by reference in their entireties.

STATEMENT OF FEDERAL FUNDING

Not applicable.

BACKGROUND OF THE INVENTION

Inflammation may be thought of as the immune system's response to an irritant. Inflammation can promote fighting an infection or healing from a wound, and is helpful in those situations. Unfortunately, in some conditions, the body reacts unnecessarily and inflammation creates equally unnecessary discomfort. Diseases such as dermatitis or psoriasis can result in inflammation of portions of the skin. Individual organs or organ systems may have conditions, such as nephritis or asthma, which are exacerbated by inflammation and for which treatment can include corticosteroids or other anti-inflammatory drugs.

As the name implies, inflammatory bowel disease ("IBD"), a group of inflammatory conditions of the gastrointestinal tract, most commonly in the colon and small intestine, are diseases with strong inflammatory components. Crohn's disease ("CD") and Ulcerative Colitis ("UC") are the major types of IBD. These diseases are chronic inflammatory conditions of the bowel and cause symptoms such as abdominal pain, diarrhea, vomiting, rectal bleeding, and can cause anemia. Currently, there are no cures for IBD but medication can be prescribed to manage the symptoms and improve quality of life for those with the disease. If symptoms of IBD are not managed, abscesses or fistulae may form in severe cases, necessitating surgical removal of parts of the colon or small intestine. Surgical intervention can significantly impact the patients' quality of life, potentially requiring the use of a colostomy bag.

There are a variety of treatments available for IBD. For mild cases, Non-Steroidal Anti-inflammatory Drugs (NSAIDs) may be prescribed; research has shown, however, that NSAIDs may have an adverse effect on IBD patients, sometimes worsening symptoms by damaging the lining of the intestines. Acetaminophen is another option but lacks effectiveness, except in mild cases.

Aminosalicylates are a family of anti-inflammatory compounds also used to treat IBD. This class of drug is effective in mild to moderate cases of IBD, but may still have side effects such as pancreatitis, headache, vomiting, fever, stomach cramping, and diarrhea.

Steroidal treatments are another class of medication used for IBD that are most useful during IBD flare ups due to their fast acting anti-inflammatory properties. However, these treatments are less effective at disease maintenance and can have significant side-effects from long term use, including weakening the immune system.

Immunomodulators are another class of treatment for IBD. These medications are effective against IBD but cause flu like symptoms and also have the side effect of weakening the patients' immune system reducing their ability to fight infection or other disease. Finally, a few biological treatments, including PDE inhibitors and monoclonal antibodies, such as Infliximab, have been used as a treatment for IBD. These biologics also have risk of side effects, including increased infections, serum sickness, and longer term side effects of decreased effectiveness of the drug, multiple sclerosis, and lymphoma.

Due to these potential short and long term side effects of managing these chronic conditions, there is a need for a treatment for IBD that provides limited short and long term side effects, is highly effective, and has a strong safety profile. Further, it would be desirable to have new agents to reduce symptoms of inflammation in other inflammatory diseases, such as asthma, nephritis, dermatitis, and psoriasis. Surprisingly, the present invention fills these and other needs.

SUMMARY OF THE INVENTION

In a first group of embodiments, the invention provides compositions comprising a unit dose of: (a) (i) an *E. coli* heat labile enterotoxin ("LT") non-toxic A subunit which inhibits ADP-ribosylation in a cell pretreated with said non-toxic A subunit when said cell is then contacted with *E. coli*. LT holotoxin, or (ii) a LT non-toxic A1 subunit which inhibits ADP-ribosylation in a cell pretreated with said non-toxic A subunit when said cell is then contacted with *E. coli* LT holotoxin, or, (iii) a combination of said non-toxic A subunit and of said non-toxic A1 subunit, and (b) a carrier which causes internalization of said non-toxic A subunit or non-toxic A1 subunit, or combination thereof, into cells. In some embodiments, the non-toxic A subunit or the non-toxic A1 subunit, or the combination of the non-toxic A subunit and the non-toxic A1 subunit does not induce intracellular cAMP accumulation in an epithelial cell. In some embodiments, the non-toxic A subunit or the non-toxic A1 subunit, or the combination of the non-toxic A subunit and the non-toxic A1 subunit activates expression and secretion of IL-6 in murine dendritic cells contacted with the non-toxic A subunit or the non-toxic A1 subunit, or the combination of the non-toxic A subunit and the non-toxic A1 subunit in vitro in a medium that supports growth of said murine dendritic cells than the said cells when contacted with LT B subunit. In some embodiments, the carrier which causes internalization of the non-toxic A subunit, non-toxic A1 subunit, or combination thereof, into cells is a LT B subunit and the unit dose is from 0.5 mg or more of non-toxic A subunit, non-toxic A1 subunit, or combination thereof and the B subunit carrier. In some embodiments, the carrier which causes internalization of the non-toxic A subunit, non-toxic A1 subunit, or combination thereof, into cells is cholera toxin B subunit ("CTB") or cholera A2 subunit/B subunit ("CTA2/B"). In some embodiments, the non-toxic A subunit, non-toxic A1 subunit, or combination thereof is chemically conjugated or recombinantly fused to the LT B subunit. In some embodiments, the non-toxic A subunit, non-toxic A1 subunit, or combination thereof is chemically conjugated or recombinantly fused to the CTB or CTA2/B subunit. In some embodiments, the carrier which causes internalization of the non-toxic A subunit, non-toxic A1 subunit, or combination thereof, into cells is a liposome or encapsulating vesicle. In some embodiments, the liposome or encapsulating vesicle is a liposome. In some embodiments, the liposome has an exterior surface and has an antibody or antigen-binding fragment or derivative thereof disposed on the exterior surface. In some embodiments, the antibody or antigen-binding fragment or derivative binds CD11c. In some embodiments, the carrier which causes internalization of the non-toxic A subunit, non-toxic A1 subunit, or combination thereof, into cells is a β-glucan. In some embodiments, the unit dose composition does not contain an exogenous antigen. In some embodiments, the non-toxic A subunit, non-toxic A1 subunit, or combination thereof, is non-toxic A subunit. In some embodiments, the non-toxic A subunit, non-toxic A1 subunit, or combination thereof, is non-toxic A1 subunit. In some embodiments, the non-toxic A subunit, non-toxic A1 subunit, or combination thereof, is a combination of non-toxic A subunit and non-toxic A1 subunit. In some embodiments, the composition is lyophilized. In some embodiments, the composition further comprises an excipient, a stabilizer, or both an excipient and a stabilizer. In some embodiments, the non-toxic A subunit, non-toxic A1 subunit, or combination thereof, has a mutation at position E112, E110, S61, or R25. In some embodiments, the mutation is selected from E112K, E112G, E112D, E110K, E110G, S61F, and R25G. In some embodiments, the mutation is of E112K. In some embodiments, the composition is in a base suitable for topical administration. In some embodiments, the composition is in a liquid. In some embodiments, the liquid further comprises a flavoring agent and a sweetener. In some embodiments, the unit dose is from about 1 mg±0.2 to 500 mg of the A subunit, A1 subunit, or combination thereof, and carrier. In some embodiments, the unit dose is from 1 mg±0.2 mg to 30 mg of the A subunit, A1 subunit, or combination thereof and carrier. In some embodiments, the unit dose is from 1 mg±0.2 mg to 20 mg±0.2 mg of the A subunit, A1 subunit, or combination thereof and carrier. In some embodiments, the composition is provided as a pill. In some embodiments, the composition is provided as a suppository.

In a further group of embodiments, the invention provides methods of reducing symptoms of inflammation in a subject in need thereof. In some embodiments, the methods comprise administering to the subject a composition comprising a therapeutically effective amount of: (a) (i) an *E. coli* heat labile enterotoxin ("LT") non-toxic A subunit which inhibits ADP-ribosylation in a cell pretreated with said non-toxic A subunit when the cell is then contacted with *E. coli* LT holotoxin, (ii) a LT non-toxic A1 subunit which inhibits ADP-ribosylation in a cell pretreated with the non-toxic A subunit when the cell is then contacted with *E. coli* LT holotoxin, or, (iii) a combination of the non-toxic A subunit and the non-toxic A1 subunit, and, (b) a carrier which causes internalization of the non-toxic A subunit or non-toxic A1 subunit, or combination thereof, into cells. In some embodiments, the non-toxic A subunit or non-toxic A1 subunit, or combination of non-toxic A subunit and non-toxic A1 subunit does not induce intracellular cAMP accumulation in an epithelial cell. In some embodiments, the non-toxic A subunit or the non-toxic A1 subunit, or the combination of the non-toxic A subunit and the non-toxic A1 subunit does not activate expression and secretion of IL-6 in murine dendritic cells contacted with the non-toxic A subunit or the non-toxic A1 subunit, or the combination of said non-toxic A subunit and the non-toxic A1 subunit in vitro in a medium that supports growth of the murine dendritic cells, compared to the cells when contacted with LT B subunit. In some embodiments, the carrier which causes internalization of said non-toxic A subunit, non-toxic A1 subunit, or combination thereof, into cells is a LT B subunit. In some embodiments, the carrier which causes internalization of the non-toxic A subunit, non-toxic A1 subunit, or combination thereof, into cells is a cholera toxin B subunit ("CTB") or cholera A2 domain and B subunit ("CTA2/B"). In some embodiments, the non-toxic A subunit, non-toxic A1 subunit, or combination thereof is chemically conjugated or recombinantly fused to said LT B subunit. In some embodiments, the non-toxic A subunit, non-toxic A1 subunit, or combination thereof is chemically conjugated or recombinantly fused to the CTB or the CTA2/B subunit. In some embodiments, the carrier which causes internalization of the non-toxic A subunit, non-toxic A1 subunit, or combination thereof, into cells is a liposome or encapsulated vesicle. In some embodiments, the carrier is a liposome. In some embodiments, the liposome is targeted to a cell antigen by an antibody or antigen-binding fragment or derivative thereof. In some embodiments, the carrier which causes internalization of the non-toxic A subunit, non-toxic A1 subunit, or combination thereof, into cells is a β-glucan. In some embodiments, the composition does not contain an exogenous antigen. In some embodiments, the non-toxic A subunit, non-toxic A1 subunit, or combination thereof, is non-toxic A subunit. In some embodiments, the non-toxic A subunit, non-toxic A1 subunit, or combination thereof, is non-toxic A1 subunit. In some embodiments, the non-toxic A subunit, non-toxic A1 subunit, or combination thereof, is a combination of non-toxic A subunit and non-toxic A1 subunit. In some embodiments, the non-toxic A subunit, non-toxic A1 subunit, or combination thereof, and the carrier is lyophilized. In some embodiments, the composition further comprises an excipient. In some embodiments, the composition further comprises a stabilizer. In some embodiments, the non-toxic A subunit, non-toxic A1 subunit, or combination thereof has a mutation in said A subunit, the A1 subunit, or both, selected from the group consisting of E112K, E112G, E112D, E110K, E100G, S61F, or R25G. In some embodiments, the non-toxic A subunit, non-toxic A1 subunit, or combination thereof has an E112K mutation in the A subunit, said A1 subunit, or both. In some embodiments, the composition is administered in water. In some embodiments, the composition is administered orally. In some embodiments, the composition is administered rectally. In some embodiments, the composition is administered intra-nasally. In some embodiments, the composition is administered parenterally. In some embodiments, the parenteral administration is intravenous. In some embodiments, the composition is administered intramuscularly. In some embodiments, the composition is administered topically. In some embodiments, the composition is administered transdermally. In some embodiments, the therapeutically effective amount is administered as an induction dose followed by one or more maintenance doses. In some embodiments, the composition is administered daily. In some embodiments, the therapeutically effective amount of said composition is from 500 μg to 500 mg. In some embodiments, the therapeutically effective amount of said composition is from 80 μg to 500 mg. In some embodiments, the therapeutically effective amount of said composition is from 1 mg to 250 mg. In some embodiments, the therapeutically effective amount of said composition is from 1 mg to 100 mg. In some embodiments, the subject in need thereof is a mammal. In some embodiments, the mammal is selected from a primate, feline, canine, bovine, equine, porcine, or ovine. In some embodiments, the primate is a human. In some embodiments, the inflammation is gastrointestinal. In some embodiments, the gastrointestinal inflammation is inflammatory bowel disease. In some embodiments, the inflammatory bowel disease is ulcerative colitis. In some embodiments, the inflammatory bowel disease is Crohn's disease. In some embodiments, the inflammation is of the skin. In some embodiments, the inflammation of the skin is psoriasis or dermatitis. In some embodiments, the inflammation is a form of inflammatory arthritis. In some embodiments, the inflammatory arthritis is rheumatoid arthritis, psoriatic arthritis, ankylosing spondylitis, or juvenile idiopathic arthritis. In some embodiments, the inflammation is of an internal organ other than the small or large intestine, bowel, or colon. In some embodiments, the internal organ is a kidney, pancreas, or liver.

BRIEF DESCRIPTION OF THE DRAWINGS

FIG. 1A. FIG. 1A presents a ribbon structure diagram of the E112K non-toxic form of enterotoxic E. coli heat-labile toxin. The diagram shows the A subunit disposed above the pentameric structure formed by five B subunits. The A1 subunit is connected to the pentameric structure of the B subunits by the A2 domain of the A subunit, which is the ribbon proceeding in a right-to-left diagonal from the top structure to the bottom structure. FIG. 1B is a photo of a SDS-PAGE gel of the A subunit, A1 domain, B subunit, and B pentamer of the E112K non-toxic form.

FIG. 2A. FIG. 2A presents brightfield images of confluent 6-well plates of epithelial cells or macrophages that were cultured with media alone or combined with E112K doses for 24 hours in 2 mls total volume. Top panel: wells cultured with media alone. Bottom photographs: wells cultivated with E112K mutant. Left side, top and bottom: cells cultured in designated media were T84 epithelial cells. Right side, top and bottom: cells cultured in designated media were macrophages. FIG. 2B. FIG. 2B presents graphs showing viability staining results of cells cultured with increasing amounts of E112K mutant, post-imaging by trypsinizing cells, washing, and staining for cytometric analyses in comparison with cells killed by heating to 95° C. for 3 mn. Data is shown as % dead cells. Left graph: T84 epithelial cells. Right side: macrophages, FIG. 2C. FIG. 2C is a graph presenting the result of a study of BALB/c mice administered the E112K mutant or different amounts of E. coli heat-labile toxin ("LT") by oral gavage. After 3 hours, the mice were euthanized and the gut/carcass weight ratios established. The results are shown in the graph. "TEAN" is a Tris buffer. (Significance by one-way ANOVA analysis with Tukey's multiple comparison post-hoc test is shown as *P≤0.05, P≤0.01 and *P≤0.001 versus controls.)

FIGS. 3A-E. FIG. 3A. Caco-2 cells cultured in 12-well plates were stimulated with E. coli heat-labile toxin ("LT"), B subunit of LT ("LTB") or E112K. After 1 day (~18 h), 3, 5, or 7 days, cells were washed extensively with phosphate buffered saline ("PBS") and lysed with RIPA buffer containing protease inhibitor. FIG. 3A shows detection by Western blot analysis of intracellular A- and B-subunits of lysates with anti-LTA and anti-LTB rabbit polyclonal sera. FIG. 3B. FIG. 3B is a graph showing intracellular cAMP pmol/ml levels in Caco-2 cells after 24 h treatment with 1 or 0.1 μg of LT, E112K, or LTB. Caco-2 cells were grown on 12-well transwell plates to confluency as measured by short circuit current (e.g., polarized epithelial cells). Cells were stimulated with LT, LTB, E112K or media. FIG. 3C. FIG. 3C is a graph showing IL-6 secretion detected in apical compartment supernatant after treatment with lug protein treatment, only observed with LT. FIG. 3D. FIG. 3D presents two graphs. The left graph in 3D shows ion secretion (% change in current), and the right graph shows monolayer integrity (% change in resistance), 1.5, 3 or 4.5 h after 0.1 μg toxin treatment measured by TEER assay. A negative current is an indicator of cellular permeability. FIG. 3E. Caco-2 cells were treated with 0.1 μg trypsin-activated LT with or without a 10 min pre-treatment with 1 μg E112K, prior to 3 h incubation and intracellular cAMP analysis. The results are presented in FIG. 3E. (Significance by one-way ANOVA analysis with Tukey's multiple comparison post-hoc test is shown as ***P≤0.001 versus naïve control.)

FIG. 4A. $1 \times 10^6$ bone-marrow derived dendritic cells were cultured in a 24-well plate stimulated with LT, LTB or E112K. After 18 h, dendritic cells were washed extensively with PBS and lysed with RIPA buffer containing protease inhibitor. Detection of intracellular A- and B-subunits was performed by Western blot analysis using whole cell lysates (WL), or cytosol, membrane and cytoskeleton cellular fractions (C, M, SK, respectively). FIG. 4A presents photographs of the Western blots. FIG. 4B. $1 \times 10^6$ bone-marrow derived dendritic cells were treated with 0.1 μg LT and/or E112K for 24 h in the presence of phosphodiesterase inhibitor prior to cell lysis and cAMP assay. FIG. 4B is a graph presenting the results. Y axis: intracellular cAMP (pmol/ml). X axis: cells treated with LT, with E112K, or untreated, respectively. FIG. 4C. FIG. 4C presents a photograph of a Western blot. $1 \times 10^6$ bone-marrow-derived dendritic cells were left untreated (lane 1), treated with 1 μg LT for 3 h (lane 2) or pre-treated with 1 μg E112K for 24 h before 3 h 1 μg LT treatment (lane 3). Detection of ADP-ribosylated protein in whole cell lysates by Western blot was performed using macrodomains. FIG. 4D. FIG. 4D is a graph presenting the results of a study showing $1 \times 10^6$ bone-marrow derived dendritic cells activation after 48 hours of LT or LPS treatment with or without a 3 hour pretreatment with 0.5 μg/ml E112K or LTB. Activation was assessed by surface staining and analysis of dendritic cell (CD11c) and co-stimulatory (CD80) markers by flow cytometry FIG. 5.

FIGS. 6A-B. Both figures: The classic dextran sulphate sodium ("DSS") chemical injury model of chronic, ulcerative colitis was induced by successive waves of 5-day drinking water treatment with 4% DSS, followed by 7-days of water in BALB/c mice. After the 2nd (day 17) or 3rd (day 29) DSS treatment, some mice were treated with 50 μg E112K by oral gavage. FIG. 6A. FIG. 6A presents two graphs. The top graph shows final weight change (day 36, % original weight), while the bottom graph shows colon length (day 38, mm) as evaluated for all groups. FIG. 6B. FIG. 6B presents H&E photographs of swiss-rolled, processed colonic mouse intestines (from day 38 collected samples). Top photograph: water treatment. Middle: DSS treatment. Bottom: DSS treatment+E112K therapy. The middle photograph shows DSS-mediated cellular infiltration (see area around black asterisk), while a moderation of DSS-mediated cellular infiltration is seen with E112K therapy (bottom photograph).

FIGS. 7A-D present a study of inflammatory bowel disease pathology in IL-10−/− colitis model. FIG. 7A. FIG. 7A is a graph showing that weight gain over time after 200 μg E112K by oral gavage in IL-10−/− female and male mice are similar to that of naïve mice. FIG. 7B. The chronic colitis model was induced in IL-10−/− mice with 7 day exposure to 200 ppm piroxicam at 6-weeks of age. Piroxicam diet (in food gel, formulated food, or powder food) induces colitis pathology at week 10. Colon histology scores were tallied using composite scoring of 4 colonic sections for type and extent of mucosal and inflammatory changes by pathologist blinded to animal treatments. As shown in FIG. 7B, 200 µg E112K by oral gavage protected the mice from induction of intestinal pathology from the piroxicam diet. FIG. 7C. FIG. 7C presents a photographic example of H&E-stained colons from piroxicam-treated animals exhibiting typical pathology including hyperplasia (top, asterisk) and ulceration of intestinal wall (bottom, asterisk), FIG. 7D. The chronic colitis model was induced in IL-10−/− mice with 7 day exposure to 200 ppm piroxicam at 6-weeks of age followed by weekly E112K treatment by intraperitoneal injection or oral gavage for three weeks. FIG. 7D presents the results in a graph comparing the colon histology score of untreated animals ("untx"), animals treated with 1 µg or with 10 µg by intraperitoneal injection (IP) or with 10 µg or with 100 µg by oral gavage ("O"). FIG. 7E is a graph presenting the results of a study of intestinal permeability. Groups of mice (n=5-6) were exposed to piroxicam and then either untreated ("untx") or treated by oral gavage of E112K weekly for three weeks ("100 µg O"). On week 10, mice were fed 4 kD FITC-Dextran at 60 mg/100 g body weight by oral gavage 3 h prior to euthanasia. Serum was collected and then analyzed for levels of fluorescent protein after 3 h oral gavage with at week 10. Significance is shown as *$P \leq 0.05$, $P \leq 0.01$ and *$P \leq 0.001$.

FIGS. 8A-D. FIGS. 8A-D show that E112K therapy improves colitis in T-Cell Transfer Colitis Model. FIG. 8A. FIG. 8A is a diagrammatic overview of the T-cell transfer model of colitis. Rag1−/− mice received 2.5e5 CD4+ CD45RB-hi T-cells by intraperitoneal injection on week 7 and were then exposed to piroxicam in food for 7 days at week 7 to induce intestinal inflammation. Some mice were left untreated, whereas others received 100 µg E112K by oral gavage on weeks 13, 16, and 18 (O E112K). After week 20, animals were euthanized. FIG. 8B. FIG. 8B is a graph showing the assessment of the euthanized animals for colitis by blinded pathology scoring. FIG. 8C. FIG. 8C is a graph showing the change in weight of the animals (as % weight change from week 7 weight). FIG. 8D. FIG. 8D is a graph comparing the stool consistency of the treated and of the untreated animals.

FIG. 9 shows a photograph of a SDS-PAGE gel of purified E112K stained with Coomasie Blue. Twenty µg of the proteins identified in the legend on the left were loaded into the well identified for the respective proteins, including native LT (LTh), E112K (lot #16001), or other mutant proteins compared to 5 µg of SeeBlue Plus 2 standard. Some proteins were exposed to 10 ng trypsin for 1 h at 37 C prior to gel analysis.

FIG. 10. FIG. 10 presents two graphs showing that mutants like E112K have minimal ability to stimulate cAMP in cultured T84 human colonic epithelial cells, in comparison with native LT. cAMP analyses were performed by testing treated cell lysates. Briefly, lyophilized lots of E112K (indicated by the numbers in parentheses) were re-suspended and tested at the various doses indicated, using 24-well seeded T84 epithelial cells pre-treated with phosphodiesterase inhibitors. After 3 h, cells were harvested, washed, and lysed for analyses of intracellular cAMP using cAMP Parameter Assay Kit (R&D Systems) at 1:20 dilutions (top graph) or 1:2 dilution (bottom graph).

FIG. 11 is a graph showing that E112K improves intestinal permeability as soon as 24 h post-treatment. The chronic colitis model was induced in IL-10−/− mice with 7 day exposure to 200 ppm piroxicam at 6-weeks of age. IL-10−/− were exposed to piroxicam for 7 days in rodent chow and then 4 days later either left untreated or treated with E112K in drinking water. Intestinal permeability was performed 1-day after treatment by analyzing serum for fluorescent protein after 3 h oral gavage with 4 kD FITC-Dextran. Significance is shown as *$P \leq 0.05$.

FIG. 12 presents two graphs showing that E112K improves disease activity index in DSS acute model of colitis in immunodeficient mice. Rag1−/− that lack functional adaptive immune system were exposed to 3% DSS in drinking water for 7 days. A group of these DSS mice were treated with oral E112K on day 5. Weight changes and disease activity index (evaluated by weight loss, fecal consistency, and blood in feces) were evaluated in animals at day 8. E112K treatment improved disease activity index, but not weight loss, indicating that at least some of E112K immunomodulatory effects are T-cell independent.

FIGS. 13A-C. FIGS. 13A-C presents graphs showing that LT-based AB5 adjuvants (LT, dmLT, mLT) mature dendritic cells and promote Th17-promoting cytokine secretion, while LTB and E112K act distinctly. FIG. 13A. $1 \times 10^6$ bone-marrow derived mouse dendritic cells were treated in triplicate for 48 h with 0.1 µg/ml test proteins before analysis of CD80 and CD86 co-stimulatory marker levels on CD11c+ gated cells. Assay was performed three independent times with representative dot blots and mean fluorescent intensity levels (MFI) from one experiment shown. Th2-promoting cytokines and Th1/Th17-promoting cytokines in culture supernatants of $1 \times 10^6$ CD11c+ purified DC cultured with 0.1 µg/ml test proteins in triplicate for 5 days. FIG. 13B. FIG. 13B is a graph presenting the results for Th2-promoting cytokines. FIG. 13C. FIG. 13C presents six graphs. The top two graphs show the results for two Th1-promoting cytokines, IL-12p70 and RANTES. The bottom four graphs show the results for four Th17-promoting cytokines, IL-1β, IL-8, IL-6, and G-CSF, respectively. Legend: "mLT" is a mutated LT with the mutation R192G in the A subunit. "dmLT" is a double-mutated LT with the mutations R192G and L211A in the A subunit.

FIG. 14 presents a proposed mechanism of E112K suppression of inflammation. Binding to surface receptors like GM1 on cells, including epithelial cells, results in release of E112K A-subunit to bind and inhibit host cells ADP-ribosylation factor (ARF). This suppresses the release of inflammatory cytokines, signaling responses, and inflammation.

DETAILED DESCRIPTION

Figure 1A:
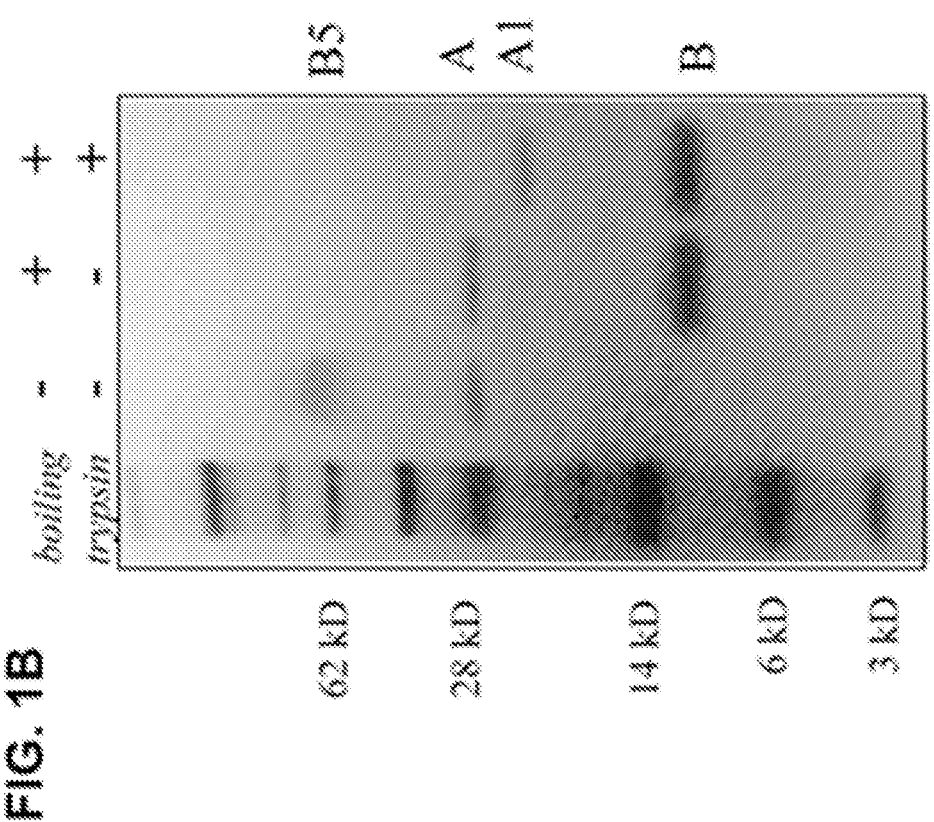
FIGS. 1A and B.
Figure 1B:
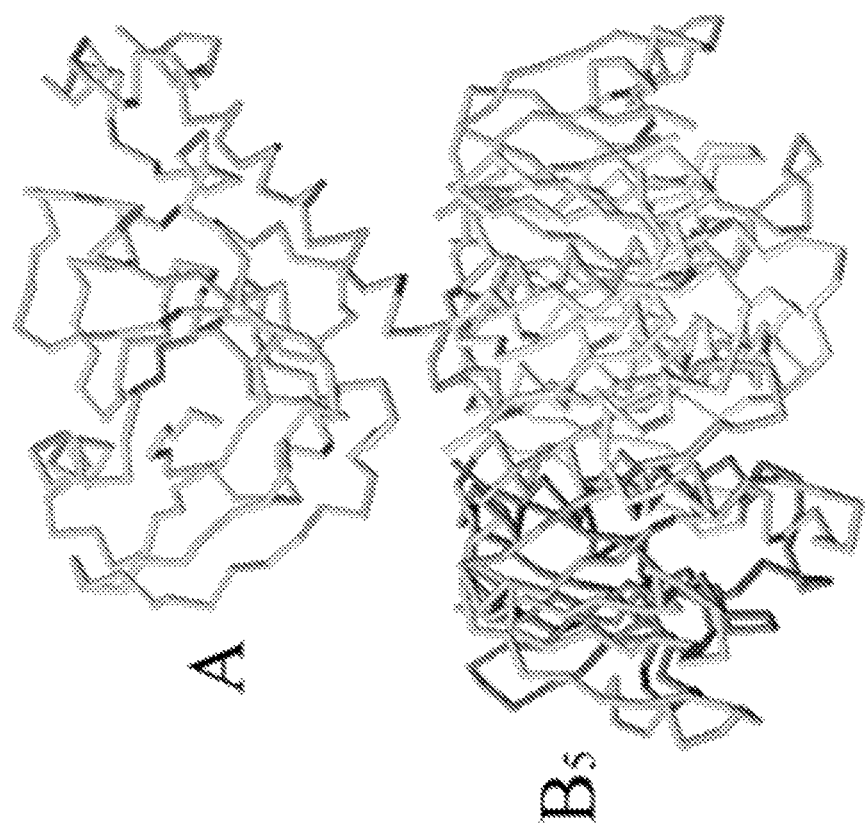
FIG. 1B.
Figure 2A:
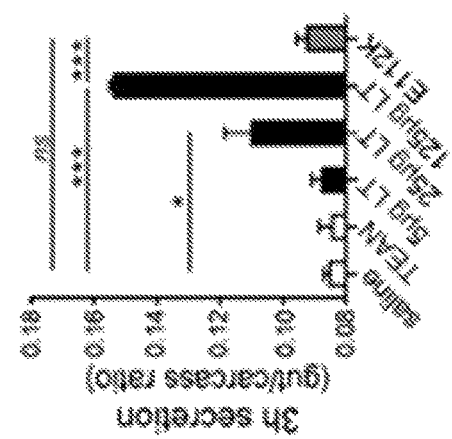
FIGS. 2A-C.
Figure 2B:
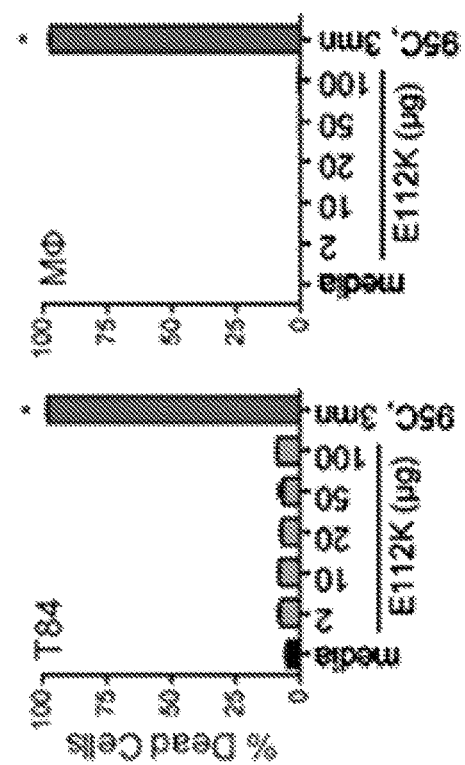
Figure 2C:
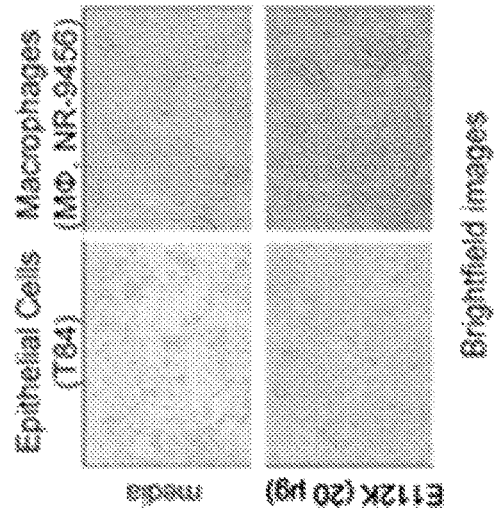

Surprisingly, it has now been discovered that non-toxic A subunits of entertoxic *E. coli* ("ETEC") heat-labile toxin ("LT") that interfere with the function of host cell ADP-ribosylation factor ("ARF") and inhibit ADP-ribosylation also inhibit the activation of dendritic cells and reduce acute and chronic inflammation, including inflammatory T-cell activity. In studies underlying the present disclosure, an exemplar detoxified A subunit and carrier that allowed it to be internalized into cells was administered to animals in several different models of inflammatory bowel disease ("IBD"). Animals treated with the exemplar construct in the studies exhibited improvements in pathology scores, showed no abnormal loss of weight, and showed normal stool consistency. In view of these results, it is believed that this detoxified A subunit, and other detoxified A subunits that likewise interfere with ART intracellular function and inhibit ADP-riboyslation will also inhibit the activation of dendritic cells, reduce acute and chronic inflammation, including inflammatory T-cell activity, and improve symptoms of IBD. Further, a study underlying the present disclosure showed rapid improvement of barrier permeability in the intestine in a murine chronic colitis model, suggesting the constructs were taken up by mucosal epithelial cells and the tissue resident myeloid cells and macrophages and ameliorated symptoms of colitis due to increased permeability. A further study in a murine model using immunodeficient mice showed that mice treated with an exemplar detoxified A subunit and carrier showed improved fecal consistency and reduced blood in feces, but did not improve weight loss, indicating that some of the detoxified A subunit effects are not T-cell dependent. Finally, studies underlying the present disclosure revealed that non-toxic A subunits have a surprisingly different effect on expression and secretion of inflammatory cytokines than do either the LT B subunit or versions of the ETEC holotoxin that act as adjuvants for antigens.

In view of these results, use of non-toxic A subunits with carriers that can cause uptake and internalization of the A subunits into dendritic cells in persons with IBD are expected to reduce and treat symptoms of IBD, in particular, intestinal or bowel inflammation, diarrhea, and blood in stool. Improvement in any one of these symptoms, or any combination of them, is expected to improve patient quality of life. Additionally, as activation of dendritic cells is a common feature of inflammatory diseases, it is believed that non-toxic A subunits that inhibit ADP-riboyslation provided in a carrier that allows internalization into cells will also reduce inflammation in conditions other than IBD. Thus, the studies underlying the present disclosure represent an important advance both in treating IBD, and more generally, in treating inflammation in other conditions in which inflammation exacerbates the condition, such as asthma, dermatitis, psoriasis, psoriatic or rheumatoid arthritis, and nephritis.

As noted, the detoxified A subunits that inhibit ADP-riboyslation are provided in a carrier that allows internalization into cells. Results of studies underlying the present disclosure indicated that the anti-IBD, anti-inflammatory results seen were due to the detoxified A subunit, not the B subunit. Thus, it is believed that the same anti-IBD, anti-inflammatory effects shown in the studies would be seen if the detoxified A subunit is delivered by other means, such as by using as a carrier the cholera toxin B subunit ("CTB"), cholera toxin A2 domain and CTB ("CTA2/B"), or encapsulating the detoxified A subunit in liposomes or other vesicles, or coupling the detoxified A subunit to other carriers that induce internalization of the detoxified A subunit into cells.

In the studies underlying the present disclosure, the detoxified A subunit (the terms "non-toxic" A subunit and "detoxified" A subunit are used as synonyms in this disclosure) was delivered to cells by the entertoxic *E. coli* ("ETEC") LT B subunit. (More precisely, the carrier in these experiments was the pentameric structure formed by five B subunits. As the individual B subunits comprising the pentameric structure are not used individually, but only as part of the pentameric structure formed by the five subunits, for convenience of reference, unless specified otherwise, the term "B subunit" herein refers to the pentameric structure formed by five B subunits of the *E. coli* LT or to the similar pentameric structure formed by five B subunits of the cholera toxin, where the discussion relates to the cholera toxin B subunit.)

In these studies, the detoxified A subunit comprised both the A1 domain of the A subunit, which is responsible in the native toxin for the toxic effects, and the A2 domain of the A subunit, which serves to non-covalently tether the A1 domain to the LT B subunit. The A2 domain is not needed if a carrier other than the ETEC LT B subunit is used, such as CTB, liposomes, and other encapsulated vesicles. Thus, at the practitioner's choice, in those embodiments, the detoxified A subunit may be just the A1 domain of the A subunit, may comprise the intact A subunit, or may comprise some molecules of the A1 domain and some of the intact A subunit.

Because enterotoxic *E. coli* heat-labile toxin is clinically important as a cause of traveler's diarrhea, there has been some investigation of ETEC LT A subunits, in combination with the LT B subunit, as vaccines against ETEC-related traveler's diarrhea, and for use as adjuvants. Detoxified A subunit mutants that inhibit ADP-ribosylation are useful as anti-inflammatory agents, but are either not useful as adjuvants to enhance a response to an antigen. With regard to vaccine formulations, one reported Phase 3 clinical trial tested LT holotoxin (intact wild-type toxin) as a vaccine administered transdermally via patch. The patch in the clinical trial contained 37.5 µg *E. coli* LT. Behrens et al., The Lancet, 2014, 14(3):197-204.

Studies in which cells were pretreated with the exemplar composition E112K and then contacted with native holotoxin did not exhibit ADP-ribosylation. The inference is that the E112K composition binds ADP-ribosylation factor ("ARF"), thereby interfering with or blocking its ADP-ribosylation activity.

As shown in FIG. 13, studies comparing E112K to native holotoxin, to LT B subunit, and to two mutated forms of holotoxin tested as adjuvants, found the effect of E112K on expression of activation markers and secretion of proinflammatory cytokines to be surprisingly different that the effect of the holotoxin, of LT B subunit, or of either of the two mutated forms of holotoxin tested as adjuvants. In contrast to holoenzyme, to LT B subunit, and to the two mutated forms of the holotoxin, E112K did not induce production of either Th1-promoting cytokines assayed or of any of the four Th17-promoting cytokines assayed. Accordingly, E112K was shown to have surprising, and surprisingly strong, anti-inflammatory properties.

Finally, in animal models of inflammatory bowel disease underlying the present disclosure, animals administered E12K exhibited less blood in stool, better fecal consistency and, in some studies, less weight loss than did animals not treated with E112K. In some embodiments, a subject with an IBD and exhibiting any one of: less blood in stool, better fecal consistency and less weight loss, when administered one of the inventive compositions or treated according to one of the inventive methods is considered to exhibit reduced symptoms of inflammation from the IBD.

Definitions

The terms "exogenous antigen" in relation to a non-toxic LT A subunit or non-toxic A1 subunit, or both, and a carrier, means that the composition of (a) the A subunit or A1 subunit or both, and (b) the carrier does not also carry with it as an additional component an antigen which will raise an immune response in the subject to which the composition is administered.

The term "carrier" as used herein in relation to a composition comprising a non-toxic LT A subunit or non-toxic A1 subunit, or both, and a carrier, refers to a molecule which, when associated with, fused to, or conjugated to the A subunit or to the non-toxic A1 subunit, facilitates entry of the A subunit or non-toxic A1 subunit into cells. The entry into the cell can be by any means of uptake, such as endocytosis, vesicle-mediated transport, an active transport pathway, or receptor-mediated uptake, depending on the particular carrier employed.

The phrase "a non-toxic LT A subunit or non-toxic A1 subunit, or both" means a composition can comprise (a) one or more non-toxic A subunits, (b) one or more non-toxic A1 subunits, or (c) one or more non-toxic A subunits and one or more non-toxic A1 subunits.

References to mutated A subunits or A1 subunits herein follow the convention of naming the amino acid residue at a particular position in the designated protein, the number of the position, and then the amino acid residue substituted for the original residue at that position. Letters representing the various amino acid residues also follow art-recognized conventions. Thus, for example, E112K describes the substitution of a lysine, K, for a glutamic acid, E, at position 112 of the LT A subunit.

The terms "effective amount" or "therapeutically effective amount" of a composition, as provided herein, refer to a nontoxic but sufficient amount of the composition to provide the desired therapeutic effect, or an amount sufficient to effect treatment of the subject, as defined below. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

The phrase "pharmaceutically acceptable," in connection with administration of a substance to a human refers to a substance that is generally safe for human pharmaceutical use. In connection with administration to a non-human animal of a particular species, it refers to a substance that is generally safe and acceptable to a non-human animal of the species in question.

As used herein, the terms "pharmaceutically acceptable carrier" and "pharmaceutically acceptable vehicle" are interchangeable and refer to a fluid vehicle for containing enterotoxin anti-inflammatories compositions that can be injected into a host without adverse effects or administered to a host by another route of administration without adverse effects, depending on the intended route of administration. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

E. *Coli* Enterotoxins and Non-Toxic LT A Subunits and LT A1 Domain

According to the website of the Centers for Disease Control and Prevention: "Enterotoxigenic *Escherichia coli* (*E. coli*), or ETEC, is an important cause of bacterial diarrheal illness. Infection with ETEC is the leading cause of travelers' diarrhea and a major cause of diarrheal disease in lower-income countries, especially among children." Certain strains of enterotoxigenic *E. coli* produce a heat-labile enterotoxin ("LT"). It has been established for many years that LT induces cAMP accumulation through binding to host cell ADP-ribosylation factor ("ARF") to initiate ADP-ribosylation of Gsα, leading to irreversible activation of adenylate cyclase and increased production of intracellular cAMP, which ultimately leads to secretory diarrhea.

LT has an $AB_5$ structure with non-covalently attached A- and B-subunits. The A-subunit causes the enterotoxic effects of the holotoxin, while the B ("binding")-subunit is responsible for cellular binding and internalization. A ribbon diagram of a partially-inactivated form of the holotoxin (discussed below) is presented in FIG. 1A, which shows the A subunit having a portion extending into a pentameric structure formed by five subunits. The 28 kD A-subunit is susceptible to cleavage by trypsin, resulting in a 21 kD A1 domain. The 56 kD B-subunit pentamer is more proteolytically stable and only breaks down into 11 kD monomers upon boiling.

The nucleic acid and amino acid sequences of both the A and the B subunits have been known for decades, as exemplified by Yamamoto et al., J. Bacterial 1987, 169:1352-57, which presents the nucleic acid and amino acid sequences of both the A and the B subunits for the form found in human isolates (shown in the paper as "LTh"), as well as the nucleic acid and amino acid sequences of the cholera toxin A and B subunits.

E112K is derived from LT, with a single amino acid substitution of a lysine residue in place of a glutamic acid residue at position 112 in the A1 domain (FIG. 1A). The mutation disrupts the active site and the ability of the molecule to ADP-ribosylate host receptor proteins. Tsuji et al, J Biol Chem, 1990, 36:22520-525. FIG. 6 of Tsuji et al. shows the nucleic acid and amino acid sequences of the entire A subunit, and notes which portions of the overall sequence constitute the A1 domain and which constitute the sequence of the A2 domain of the A subunit.

As shown in the studies reported in the Examples, below, E112K protein is non-toxic and exhibits no alteration in cell viability of culture treated macrophages or epithelial cells (FIGS. 2A, 2B). A classic characteristic of native LT is induction of fluid secretion during enterotoxigenic *Escherichia coli* ("*E. coli*"), or "ETEC" infection or with purified LT alone. However, the mutation in E112K prevents induction of intestinal fluid secretion (FIG. 2C).

The E112K construct used in the Examples was the A subunit with an E112K mutation, tethered through the A2 domain to an ETEC LT B subunit, which acted as the carrier to allow internalization of the A subunit and the B subunit into cells, such as dendritic cells. References to "E112K" in the Examples refer to this construct. References in other sections of the disclosure refer to this construct when referring to the Examples, but in other places refer either to this construct or to an A subunit or A1 subunit, which may be paired either with an ETEC LT B subunit, or with a different carrier, such as a cholera toxin B subunit ("CTB"), A2 domain/B subunit ("CTA2/B"), a liposome, and other carriers described elsewhere in this disclosure.

E112K has (1) no ability to ADP-ribosylate host receptor proteins, (2) no ability to induce intracellular cAMP accumulation in epithelial cells, and (3) no ability to act as a robust adjuvant for co-administered antigens. Further, as shown in the Examples and in FIG. 13, studies underlying the present disclosure showed that E112K had a surprisingly different effect on the expression of activation markers and secretion of pro-inflammatory cytokines than did either the B subunit or of mutated forms of the A subunit that have been shown to be able to adjuvant responses to antigens. In particular, as shown in FIG. 13, mouse dendritic cells contacted with E112K in vitro in a medium supporting dendritic cell growth, showed do not express and secrete IL-6 or other pro-inflammatory cytokines. For purposes of this disclosure, a "non-toxic A subunit" or a "non-toxic A1 domain" means an A subunit or A1 domain which, when delivered to cells, shares these properties.

Several other mutated forms of the A1 domain are believed to share these functional properties. These forms are: E112G, E112D, E110K, E110G, E110D, S61F, and R25G. Given these shared functional properties, it is believed that each of these other mutated forms of the LT A subunit and of the A1 domain are non-toxic and will also be unable to induce inflammatory cytokines when internalized into a cell. It is therefore believed that each can be used as anti-inflammatory agents. Since it is the A1 domain of the LT A subunit that is responsible for the toxic effect of LT (as noted, the A2 domain serves as a tether to the B subunit, and is not believed to participate in interference with ARF function or inhibition of ADP-ribosylation), references to mutations in the A1 domain or subunit also refer to mutations in the A subunit comprising both the A1 domain and the A2 domain. Further, for convenience of reference, reference herein to "A1 subunit" when referring to the E. coli LT means the A1 domain of the LT A subunit, or of mutated forms of the LT A1 domain of the A subunit, as required by context.

While the eight mutants described above are exemplary of mutations in the A1 subunit that remove the ability of the A1 subunit to induce diarrhea and to avoid other adverse effects, they are only some of the variations in the A subunit or A1 subunit that are expected to have these effects. For example, in E112K, the acidic amino acid residue E, glutamic acid, which is negatively charged at physiological pH (all references to charge in this section refer to charge while in an aqueous solution at physiologic pH), is replaced with a K, a basic amino acid that is positively charged, while in E112D, the glutamic acid has been replaced with D, aspartic acid, another negatively charged residue. This suggests that E112, which is at the active site of the A1 subunit, is particularly sensitive to mutations and that the toxic properties of A1 would also be abrogated at least by substitution of the E with another positively charged amino acid, arginine ("R"). Similarly, in S61F, the uncharged, polar serine ("S") residue at position 61 is replaced with F, phenylalanine, an amino acid with a hydrophobic side chain terminating in a phenyl ring, suggesting that substituting the S with a tyrosine ("Y") residue, whose side chain also terminates in a phenyl ring, but with a hydroxyl attached to the ring, will also result in inactivation of the A1 subunit's enzymatic properties. In the R25G detoxified A1 subunit, the arginine, R has been substituted by a small, uncharged amino acid, G, glycine, suggesting that substituting the positively charged R with either of the negatively charged residues E or D will also result in inactivation of the A1 subunit. Other substitutions will readily suggest themselves to persons of skill in the art and can readily be tested to see if they result in (1) inhibition of ADP-ribosylation of host receptor proteins, (2) no ability to induce cAMP in epithelial cells, and (3) no ability to act as a robust adjuvant for co-administered antigens. In some embodiments, therefore the inventive compositions and methods contemplate use of detoxified forms of the A1 subunit sharing these three properties. Other mutations of residues at the active site of the A subunit's ADP-ribosylation activity that confer these properties are also comprehended.

In some embodiments, the detoxified A1 subunit is E112K. In some embodiments, the detoxified A1 subunit is E112G. In some embodiments, the detoxified A1 subunit is E112D. In some embodiments, the detoxified A1 subunit is E110K. In some embodiments, the detoxified A1 subunit is E110G. In some embodiments, the detoxified A1 subunit is E110D. In some embodiments, the detoxified A1 subunit is S61F. In some embodiments, the detoxified A1 subunit is R25G.

Delivery of a Subunit by Means Other Than the LT B-Subunit

The B-subunit mediates binding of the holotoxin to cells and internalization into them. The B-subunit binds to ganglioside receptors, such as $GM_1$ (monosialotetrahexosylganglioside) on gut epithelial cell membranes and dendritic cells. There are several types of B-subunits, Type I and II A and B, which differ in amino acid sequence and the extent to which they bind different ganglioside receptors. See, e.g., Tinker et al., Infection and Immunity, 2005, 73(6): 3627-55. It is believed that the anti-inflammatory effects seen in the studies underlying the present disclosure are due to the detoxified A1 subunit and not to the B subunit. Thus, it is believed that the potent anti-inflammatory effects shown in the studies reported in the Examples can be achieved by delivering a detoxified A1 subunit to dendritic cells and other cells of interest using means of delivery other than an LT B subunit.

In some embodiments, it is contemplated delivering a detoxified A1 subunit to cells of interest using the pentameric cholera toxin B subunit ("CTB") or the non-toxic cholera toxin CTA2/B.

Chimeras have been made and have demonstrated the efficacy of CTB as a carrier for antigens for some thirty five years, as exemplified by, e.g., McKenzie and Halsey, J Immunol, 1984, 133 (4) 1818-1824 (horseradish peroxidase (HRP) covalently attached to CTB was shown to raise order of magnitude greater amounts of anti-HRP antibody than HRP or CTB alone), In 1990, a genetic construct of nucleic acid encoding glycosltransferase at the N-terminal of CTB was made and shown to maintain structure and function of CTB. The authors stated the study "demonstrated a complete system for constructing, expressing, and purifying cm chimeras." Dertzbaugh et al., Infect. Immun. 1990, 58(1):70-79, at p. 78. By 2001, researchers in the area were able to state "It is well established that CTB is a highly efficient carrier molecule for the induction of mucosal antibody responses . . . as well as for the induction of mucosally induced systemic T-cell . . . and systemic B-cell . . . tolerance." George-Chandy, et al., Infect Immun. 2001, 69(9):5716-25 ("George-Chandy"), at p. 5723. (Citations omitted. George-Chandy reported in their study that antigen chemically conjugated or genetically fused to CTB "dramatically lowers the threshold concentration of antigen required for immune cell activation." See, Abstract.)

Both CTB and constructs of the A2 domain of cholera toxin ("CTA2") in combination with CTB ("CTA2/B"), have been shown to deliver exogenous proteins to cells. See, e.g., Li et al., Infect. Immun. 2004, 72:7306-7310; Tinker et al., Toxins 2014, 6(4), 1397-1418 (West Nile Virus DIII-CTA2/B chimera shown to be immunogenic after intranasal delivery). CTB has been used to deliver antigens orally and to serve as an adjuvant for mucosal delivery of antigens intranasally, rectally, and vaginally. See, e.g., Holmgren, et al., Vaccine, 1993, 11(12):1179-84; Hajishengallis et al., J Immunol, 1995, 154(9):4322-4332; Langridge et al., Current Opin Investig Drugs, 2010, 11(8):919-928. George-Chandy, supra, reported that chemically conjugating antigen to CTB or expressing the antigen and CTB as a fusion protein resulted uptake of antigen into cells through the GM1 ganglioside receptor, showing that proteins conjugated or fused to the CTB are taken into the cell.

In short, reports over the past three decades have shown that work has shown that a variety of proteins have been successfully recombinantly fused or chemically conjugated to CTB and CTA2/B and successfully delivered into target cells both in vitro and in vivo. It is therefore expected that non-toxic LT A subunits that bind to ARF can be genetically fused or chemically conjugated to CTB or to CTA2/B by the methods developed over the past three decades. It is further expected that such fusions or conjugates will be delivered into cells just like the numerous fusions and constructs already demonstrated to deliver proteins into cells, as exemplified by the antibodies that have been raised against the proteins. Since the LT A2 subunit serves as a linker to the B subunit, but does not participate in interaction with ARF, it is expected that the A2 portion of the A subunit can be omitted in such chimeras, reducing the size of the LT protein to be fused or conjugated to CTB or CTA2/B.

In some embodiments, the detoxified A subunit can be loaded into liposomes or other encapsulating vesicles. Loading therapeutic agents into liposomes has been known since the 1980s. See, e.g., Woodle and Storm, eds., LONG CIRCULATING LIPOSOMES Old Drugs, New Therapeutics, (Springer-Verlag Berlin Heidelberg, 1998), Lasic and Papahadjopoulos, eds., MEDICAL APPLICATIONS OF LIPOSOMES (Elsevier Science B.V., Amsterdam, 1998), Gregoriadis, G., ed., LIPOSOME TECHNOLOGY $2^{ND}$ EDITION, ENTRAPMENT OF DRUGS AND OTHER MATERIALS, vols, I and II (CRC Press, Inc., Boca Raton, FL, 1993). Liposomes or other encapsulating vesicles known in the art are typically taken up by myeloid cells and endocytosed, delivering the inventive compositions into cells of the immune system that can initiate reduction of inflammatory symptoms.

In some embodiments, the liposomes or other encapsulating vesicles can be targeted to cell types of interest by tethering antibodies or fragments (e.g., Fab, F(ab')2, or variable region fusion proteins (e.g., single chain variable fragments, or "scFv") of antibodies that bind antigen to the exterior of the liposomes. Methods of targeting liposomes to target cells by tethered antibodies, antigen-binding portions, or fusion protein derivatives thereof, such as Fab, F(ab')2, and scFvs, have been known since at least the early 2000s, as exemplified by, e.g., U.S. Pat. Nos. 6,210,707 and 6,214,388. In some embodiments, the antibodies or antigen-binding fragments or single chain variable fragments thereof bind CD11c. According to Martin, A., in D. Dabbs, ed., DIAGNOSTIC IMMUNOHISTOCHEMISTRY $3^{rd}$ Edition (2011, Saunders, Philadelphia), CD11c is a type I transmembrane protein that is expressed on monocytes, granulocytes, a subset of B cells, dendritic cells, and macrophages. Internalization of the inventive compositions into any of these cell types is expected to result in reduced inflammation and consequent alleviation of symptoms of inflammation.

Conditions for Which Mutant Enterotoxins Can Be Used as Anti-Inflammatory Agents It is anticipated that symptoms of many inflammatory diseases and conditions can be ameliorated or treated by the inventive methods and compositions.

As enterotoxic E. coli (ETEC") and cholera affect the mucosal lining of the intestinal tract, the B subunits of their toxins are particularly good for carrying detoxified A subunits to mucosal surfaces. Thus, embodiments of the inventive compositions and methods are particularly suited for ameliorating inflammation in the gastrointestinal tract. Chronic inflammation can occur at various sites within the gastrointestinal tract. See, e.g., Bamford, K., FEMS Immunology & Medical Microbiology, 1999, 24(2)161-168. It is contemplated that in some embodiments, the inventive compositions and methods can be used transmurally to ameliorate symptoms of inflammation throughout the entire tract, while in other embodiments, they can be used to ameliorate symptoms at particular sites or in particular segments, such as the bowel or colon, depending on the form and route of administration. For example, compositions administered orally in liquid form would be expected to travel, and ameliorate symptoms, along the entire tract, while compositions administered in the form of a suppository would be expected to ameliorate symptoms in the rectum. In some embodiments, an endoscope or similar instrument can be used to deliver the inventive compositions to an affected site within the large or the small intestines, or both. For example, a colonoscope can be used to deliver an inventive composition to the junction of the ileum and the colon.

In some embodiments, the gastrointestinal inflammation to be ameliorated is inflammatory bowel disease (sometimes referred to herein as "IBD"). According to the CDC, in 2015, an estimated 1.3% of U.S. adults, or over 3 million individuals, had been diagnosed with IBD, a 50% increase from the number with IBD in 1999. See also, Dahlhamer, et al., MMWR Morb Mortal Wkly Rep., 2016, 65(42):1166-1169.

Two major forms of IBD are Crohn's disease (sometimes referred to herein as "CD") and ulcerative colitis (sometimes referred to herein as "UC"). In some cases, it cannot be determined if a patient's IBD is CD or UC. In such cases, the patient may be diagnosed with indeterminate colitis. According to the Crohn's and Colitis Foundation of America ("CCF"), CD can affect any portion of the gastrointestinal tract, but most commonly affects the junction of the ileum and the colon mentioned above. The CCF further states that inflammation due to CD can occur in patches and extend through the entire thickness of the intestinal wall. In contrast, the CCF states that UC occurs only in the colon and rectum and inflammation affects only the inner lining of the tract. Both diseases cause abdominal pain, diarrhea, and a feeling of urgency to empty the bowels, and can cause rectal bleeding. CD can cause fistulas and strictures in the intestines. UC and, less commonly, CD, can cause toxic megacolon, in which severe inflammation causes the colon to enlarge, which can lead to nerve and muscle damage and almost complete paralysis of the affected portion. Both UC and CD can also cause the bowel to perforate.

Both CD and UC have been extensively studied. Baumgart and Sandborn, The Lancet, 2012, 380(9853): 1590-1605, provides a review of the etiology, diagnosis, and treatment of CD. See also, Hart an Ng, Medicine, 2015, 43(5):282-290. UC is reviewed in, e.g., Ho et al., Medicine, 2015, 43(5):276-281. UC also occurs in children; pediatric UC is discussed in, for example, Turner, Inflam. Bowel D is, 2011, 17(1):440-49. Extensive information regarding UC and CD are also available in standard texts, such as Friedman and Blumberg, "Inflammatory Bowel Disease," in Jameson et eds., HARRISON'S PRINCIPLES OF INTERNAL MEDICINE, $20^{th}$ Ed. (McGraw Hill Education, New York, 2018).

In animal studies underlying the present disclosure, colitis scoring was conducted as described in Chassaing, et al., Curr Protoc Immunol, 2014, 104(1): 15.25.1-15.25.14. There are a number of indices for grading UC activity and severity in humans, which use criteria such as histology, inflammation, and endoscopic examination. D'Haens et al., Gastroenterology, 2007, 132:763-786, present a review of a number of activity indices and efficacy end points for clinical trials for UC in adults. The reference reviews ten indexes for measuring the severity of UC (e.g., the Truelove and Witts Severity Index, the Powell-Tuck Index, the Seo Index), and nine endoscopic measures of disease activity (e.g., the Truelove and Witts Sigmoidoscopic Assessment, the Baron Score, and the Modified Baron Score). A scoring system proposed by Geboes et al., Gut. 2000, 47:404-409, provides a scale for grading inflammation. According to Jauregui-Amezaga, et al., Jr Crohn's and Colitis, 2017, 11(3):305-313, the Geboes score is one of the most commonly used histological scores for grading UC, but is somewhat complicated, and proposed a simplified version. Xie et al., Gastroenterology Report, 2018, 6(1):38-44, compares the Ulcerative Colitis Endoscopic Index of Severity (UCEIS) and the Mayo Endoscopic Score (MES), both of which were developed as objective methods to measure endoscopic severity, as predictors of the need for colectomy. Travis et al., Aliment. Pharmacol. Ther., 2011, 34:113-24, review the different definitions of remission of UC used in various trials and propose a standard definition based on clinical symptoms and endoscopy, with histopathology as a third dimension.

While practitioners have not agreed on a universal system for measuring improvement or remission of UC, all the indices mentioned above are intended to provide measures of improvement or worsening of the condition and all are accepted by some portion of the medical community. For purposes of the present disclosure, it is contemplated that a reduction of activity score in any of the activity indexes noted in the references above, or a reduction of the endoscopic activity score as set forth in any of the indexes set forth in those references indicates an amelioration of symptoms of inflammation due to UC.

In view of the reduction of T cell regulatory activity seen in studies underlying the present disclosure, it is believed that, in addition to IBD, embodiments of the inventive compositions and methods can be used to reduce or ameliorate symptoms of inflammation in a number of other conditions in which relieving symptoms of inflammation would be of benefit to the patient. In some embodiments, the conditions are ones in which other anti-inflammatory agents have been found to be helpful. For example, in some embodiments, the inventive compositions can be administered to persons suffering from asthma, in addition to, or in place of, the inhaled corticosteroids currently used as long-term asthma control medications, or as a quick-relief agent to reduce airway inflammation during severe asthma. It is contemplated that in these uses, the inventive compositions will be administered by inhaler, using devices similar to those used to deliver current asthma medications.

In some embodiments, the inventive compositions and methods can be used to relieve inflammation in joints caused by various forms of inflammatory arthritis, such as rheumatoid arthritis, psoriatic arthritis, ankylosing spondylitis, and juvenile idiopathic arthritis. In these embodiments, it is contemplated that the inventive compositions will be mixed into formulations suitable for carrying the compositions into the skin. Creams and ointments for introducing therapeutic agents into the skin are well known. Other conditions for which topical application is expected to be useful are dermatitis and psoriasis. It should be noted that a transdermal patch containing 37.5 µg E. coli LT as a vaccine was tested in clinical trials and found to shorten episodes of traveler's diarrhea and result in fewer loose stools (Frech et al., Lancet 2008,371(9629):2019-25). A Phase 3 study of a skin patch containing 37.5 µg E. coli LT found that the LT was delivered effectively and was immunogenic. Behrens et al., The Lancet, 2014, 14(4197-204, showing that LT can be delivered through the skin into antigen presenting cells. The inventive compositions and methods are also expected to also be useful in reducing inflammation of internal organs, including conditions including nephritis, pancreatitis, and liver inflammation, as well as systemic inflammatory diseases, such as lupus. In these embodiments, the compositions are conveniently delivered to the organs by intravenous (IV) infusion.

Formulations

Formulations of the inventive compositions will depend in part on the site of the inflammatory condition whose symptoms are to be treated or ameliorated, and the contemplated route of administration. In the murine studies reported in the Examples, detoxified LT E112K administered in drinking water was shown to be effective in several different murine models of inflammatory bowel disease. Based on these studies, formulations for reducing inflammation in IBD, including Crohn's disease and ulcerative colitis, could be as simple as providing a subject in need thereof water containing a composition of a detoxified A subunit and a carrier of choice. The water preferably contains a small percentage of NaCl or another pharmacologically acceptable salt to maintain conformational stability of the proteins and to maintain the proteins in solution. Preferably, the salt is present at 0.1M. In some formulations, the detoxified A subunit and carrier of choice may be provided in lyophilized form, and reconstituted in water prior to being taken orally by the subject. These formulations may be given orally or, for example, may be administered through an endoscope to a desired site in the gastrointestinal tract.

For oral administration, FDA-approved flavoring ingredients and sweeteners that are compatible with the detoxified A subunit and carrier of choice may be added. It is unlikely that any particular generally used flavoring ingredients or sweeteners are not compatible with administration of the detoxified A subunit and carrier of choice, but any particular combination can be readily tested by performing two parallel studies following the protocol described in Example 5, below, or in Example 6, below, one in which the detoxified A subunit and carrier of choice are provided in water and one in which the detoxified A subunit and carrier of choice are provided in water with the combination of flavoring ingredient and sweetener to be tested, and comparing the results. If the addition of the flavoring ingredient and sweetener to the water with the detoxified A subunit and carrier of choice results in reducing the benefit to the mice seen by use of the detoxified A subunit and carrier of choice in water alone, that combination of flavoring agent and sweetener is not a compatible combination with the detoxified A subunit and carrier of choice. In similar formulations, the composition can be provided as syrups or suspensions.

In some embodiments, the detoxified A subunit and carrier of choice may be administered in a suitable oral dosage form, such as a pill, capsule, tablet, lozenge, pastille, pellet, medicated chewing gum, powder, solution, suspension, wafer, or syrup. Making such oral dosage forms is well known in the art, and it is expected that persons of skill are familiar with the considerable literature and guidance that exists, as exemplified by texts such as Gennaro, A., REMINGTON'S PHARMACEUTICAL SCIENCES, 18$^{th}$ Ed., (1990), Rowe, Shesky and Quinn, eds. HANDBOOK OF PHARMACEUTICAL EXCIPIENTS, 6$^{th}$ Ed. (Pharmaceutical Press, London, 2009) and L. Allen, ed., REMINGTON: THE SCIENCE AND PRACTICE OF PHARMACY, vols I and II, 22$^{nd}$ Ed. (Pharmaceutical Press, Philadelphia, 2012).

In addition to the detoxified A subunit and carrier of choice, the formulations may include one or more pharmaceutically acceptable excipients, stabilizers, binders, lubricants, tillers, buffers, antioxidants, such as ascorbic acid, preservatives (such as octadecyldimethylbenzyl ammonium chloride; hexamethonium chloride; or benzalkonium chloride), monosaccharides, disaccharides, and other sugars or carbohydrates, including glucose, mannose, sucrose, mannitol, trehalose or sorbitol, low molecular weight polypeptides, proteins, such as serum albumin or gelatin, hydrophilic polymers such as polyvinylpyrrolidone, chelating agents such as EDTA, and salt-forming counter-ions such as sodium. In some embodiments, the pills, capsules, or tablets may be formulated to be taken bucally (against the cheek) or sublingually (under the tongue) or to be orally disintegrating. In some embodiments, the compositions may be included in a film that dissolves and releases the compositions when administered buccally or sublingually, or in a spray that is so administered to the mouth or to the nasal cavity. In some embodiments, the pill, capsules, or tablets may be formulated as modified release dosage forms, including delayed, extended, sustained, pulsed, or fast release forms.

Formulations intended for application to the skin are typically in an ointment base of a thick oil in a 80% oil to 20% water mixture with a high viscosity. A number of bases, such as beeswax, hydrocarbon bases, such as ceresine, and vegetable oil bases are known and can be selected depending on the particular properties of penetrability, stability, solvent property and release of medicament desired by the practitioner. The inventive compositions and methods can also administered topically in the form of gels or in transdermal patches, such as those used in the clinical trials testing LT as a vaccine for enterotoxic *E. coli* discussed in the preceding section.

Dosing and Administration

For purposes of the inventive methods, an "effective amount" or a "therapeutically effective amount" of a composition comprising a detoxified LT A subunit refers to an amount that, alone or in combination with further doses, produces the desired response, e.g., alleviation or elimination of inflammation. This may involve decreasing the amount of inflammation only temporarily or only briefly, so long as it is measurable. This can be measured by standard methods, such as the UC activity scores and endoscopy score indices discussed in a preceding section.

The "therapeutically effective amount" will depend on the particular condition being treated, the severity of the condition, patient characteristic such as age, physical condition, size, gender, and weight, the duration of treatment, the nature of concurrent therapy, if any, the specific route of administration, and similar factors. These factors are well known to treating physicians, who are trained to make decisions regarding treatment regimens and dosages based on these and similar criteria. It is generally preferred that the patient be administered the highest safe dose according to clinical judgment, but it is understood, as with many therapeutics, that the patient may wish to take a lower dose for any of a variety of reasons. It is also understood that the practitioner's decision about how much to prescribe to a particular patient will be guided by information obtained during clinical trials of the compositions.

In some embodiments, the practitioner may evaluate a patient for the severity of UC before commencing administration of an induction dose and then reevaluate the patient following the induction dose to determine if there has been a desired clinical effect, as shown by any of endoscopic improvement, endoscopic remission, clinical response, an improvement in scoring under the practitioner's choice of disease activity index or endoscopic index, rectal bleeding subscore, endoscopic subscore, histologic improvement, and combinations thereof.

For topical administration or administration by injection, it is contemplated that the dose range will be from about 1 μg (with "about" here meaning ±0.1 μg) to about 5 mg (with "about" here meaning ±0.2 mg. All dosages stated herein refer to the amount of detoxified A subunit and carrier.) In some embodiments in which the amount of detoxified A subunit and carrier administered is 100 μg or less, the composition administered does not also contain an exogenous antigen to which the practitioner wishes to raise an immune response. In some embodiments in which the amount of detoxified A subunit and carrier administered is 75 μg or less, the composition administered does not also contain an exogenous antigen to which the practitioner wishes to raise an immune response. In some embodiments in which the amount of detoxified A subunit and carrier administered is 50 μg or less, the composition administered does not also contain an exogenous antigen to which the practitioner wishes to raise an immune response.

For oral administration, it is contemplated that the dose range will be from about 100 μg (with "about" here meaning ±5 μg) to about 500 mg of detoxified A subunit and carrier (with "about" here meaning ±2 mg.) For some conditions causing the inflammation being treated, compositions comprising the detoxified A subunit and carrier may be administered in a single dose intended to reduce symptoms of inflammation, while in others, the compositions will be administered in multiple doses. In some embodiments, it is contemplated that multiple doses of compositions comprising the detoxified. A subunit and carrier will be administered in an larger "induction dose," followed by one or more smaller "maintenance doses." In these embodiments, it is contemplated that the larger induction dose will induce an initial reduction of symptoms of inflammation, while the following, maintenance, doses will be at a lower dosage to keep the inflammatory symptoms in check and, preferably, wholly suppressed.

For amelioration of inflammation due to UC or CD, which present as chronic conditions, maintenance doses may be administered, for example, daily, every other day, biweekly, weekly, or every two weeks, for a period of months, or indefinitely. If maintenance doses alone are not keeping symptoms of inflammation in check, one or more additional induction doses may be administered to reduce or bring symptoms of inflammation under control before returning to, and continuing with, maintenance doses. For example, if the inflammatory condition is UC, and the patient's UC activity score has regressed from one achieved after an induction dose, the patient can administered one or more additional induction doses. The additional doses can be administered daily, biweekly, or weekly until clinical improvement is seen. In some embodiments, the induction doses may be continued until there is a clinical remission as determined, for example, by endoscopic examination or the patient's subjective evaluation of quality of life, including reduction or lack of tenesmus, whereupon the patient can be started on, or returned to, maintenance doses. It is contemplated that induction doses administered for UC, CD, or other IBDs, will be 1 mg to 500 mg, about 2-400 mg, about 2-300 mg, about 5-200 mg, about 5-150 mg, about 5-100 mg, about 5-50 mg, or about 5-25 mg with each succeeding range being more preferred than the one before it and "about" in this context meaning ±1 mg. It is further contemplated that maintenance doses will range from 1 mg to 300 mg, 1 mg to 200 mg, about 2-200 mg, about 2-150 mg, about 2-100 mg, about 2-75 mg, about 2-50 mg, about 2-40 mg, about 2-30 mg, about 2-20 mg or about 2-10 mg, with each succeeding range being more preferred than the one before it and "about" in this context meaning ±1 mg.

In the animal studies reported in the Examples, mice with different models of IBD showed reduction of symptoms when administered daily detoxified A subunit and carrier in water which contained 0.3% NaCl. Accordingly, in some embodiments, the patient may take daily doses of detoxified A subunit and carrier in a suitable liquid, such as water. In some embodiments, a dose for daily administration may be 1 mg to 500 mg, 1 mg to 300 mg, 1 mg to 200 mg, about 2-200 mg, about 2-150 mg, about 2-100 mg, about 2-75 mg, about 2-50 mg, about 2-40 mg, about 2-30 mg, about 2-20 mg or about 2-10 mg, with each succeeding range being more preferred than the one before it and "about" in this context meaning +1 mg.

Figure 4A:
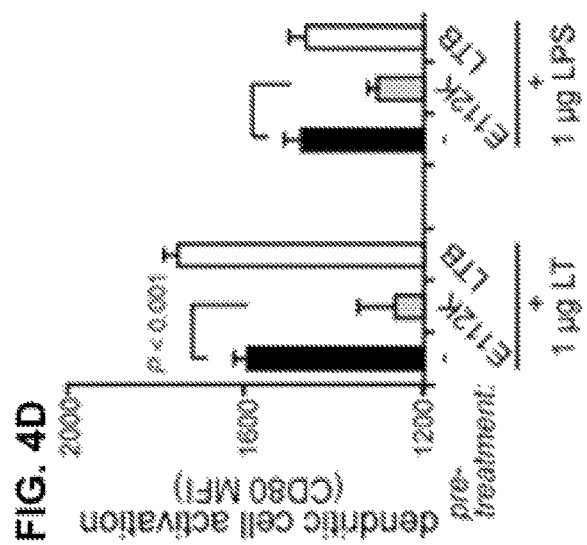
FIGS. 4A-D.
Figure 4B:
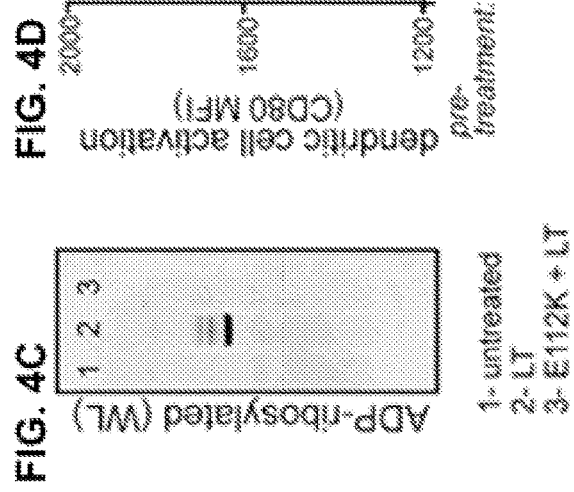
Figure 4C:
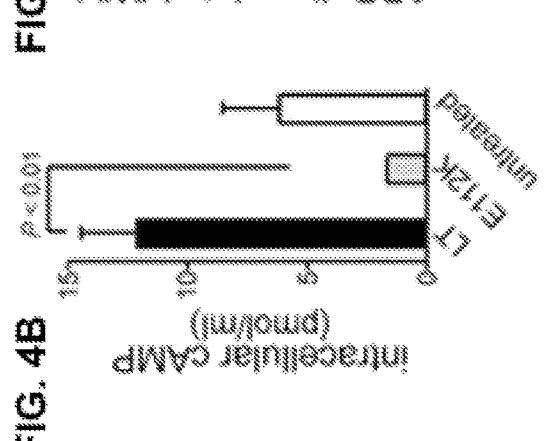
Figure 4D:
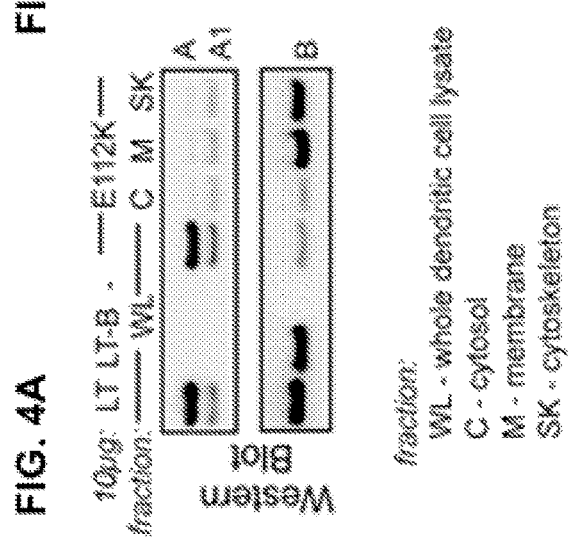
Figure 5:
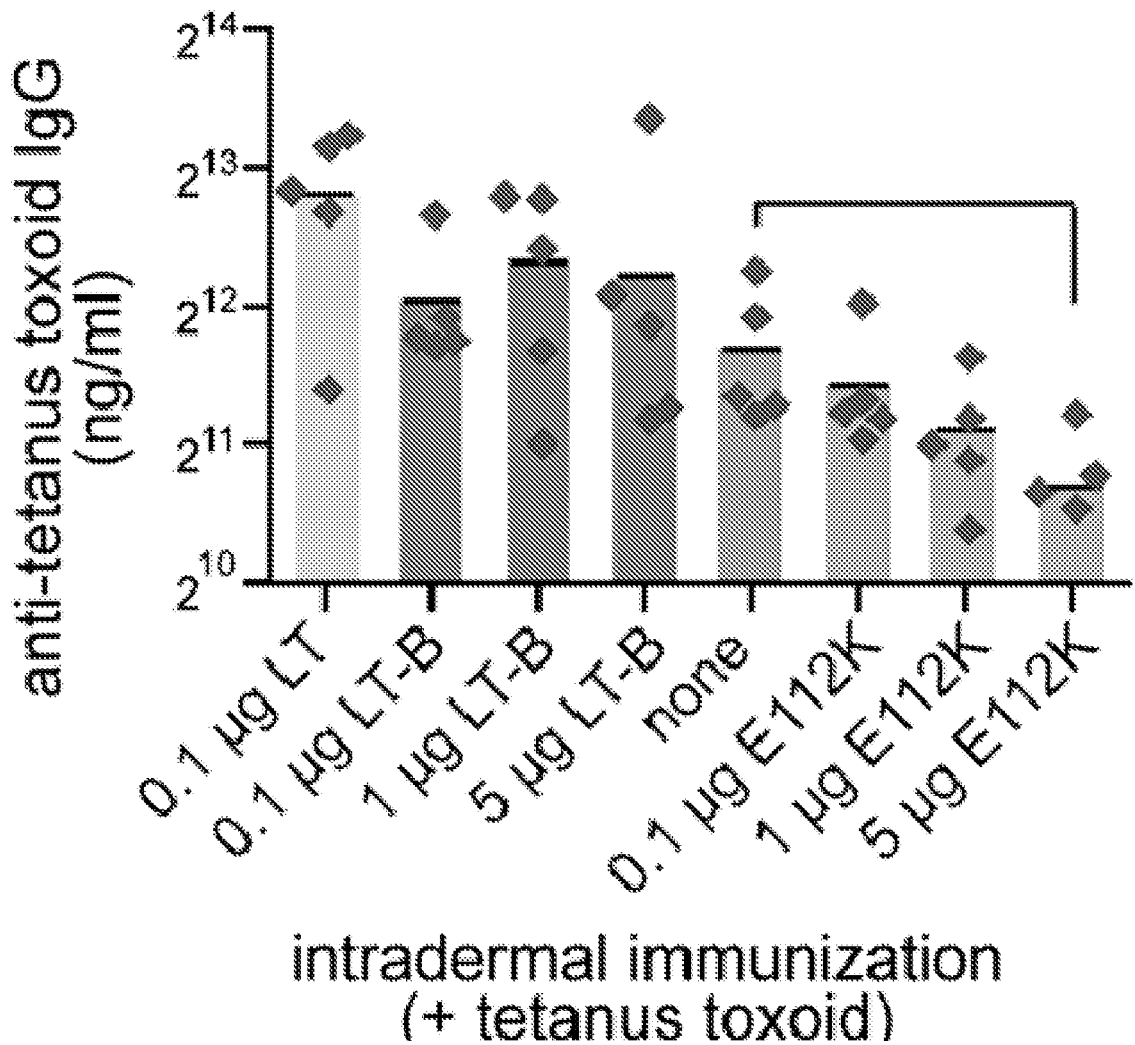
FIG. 5 is a graph presenting the results of a study in which BALB/c mice were immunized intradermally with 50 μl containing 10 μg tetanus toxoid and 0.1-5 μg LT, LTB, E112K or no adjuvant (designated on graph as "none"). After 21 days, serum was collected and analyzed by ELISA for presence of anti-tetanus toxoid antibodies.
Figure 7A:
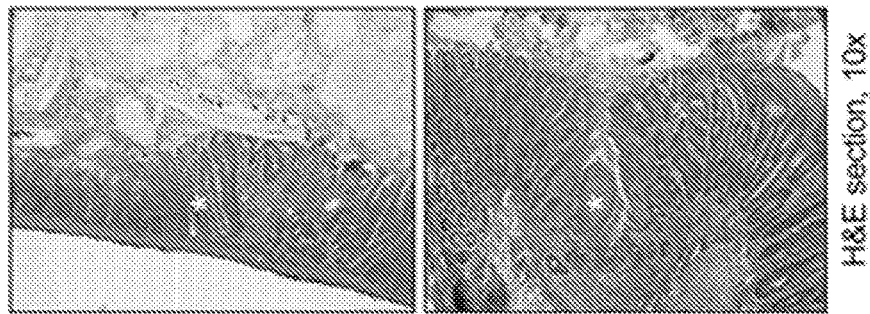
FIGS. 7A-D.
Figure 7C:
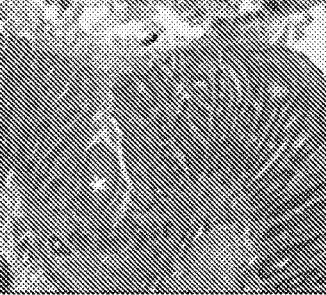
Figure 7B:
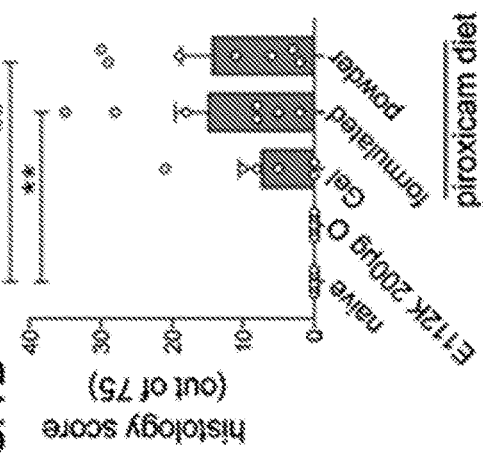
Figure 7D:
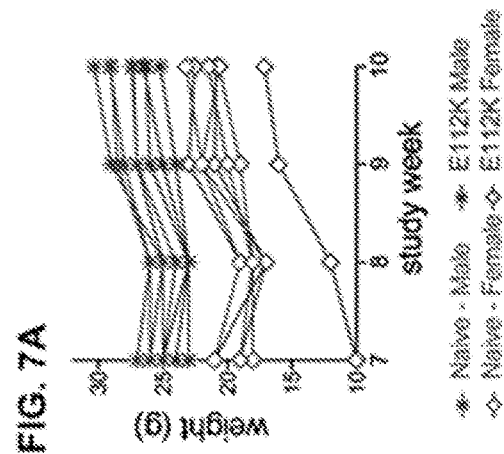
Figure 7E:
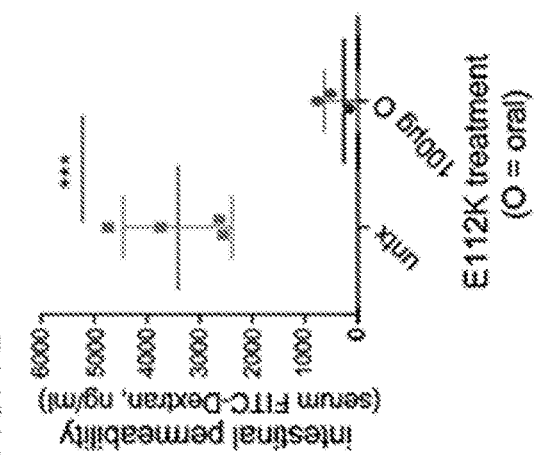
FIG. 7E.
Figure 9:
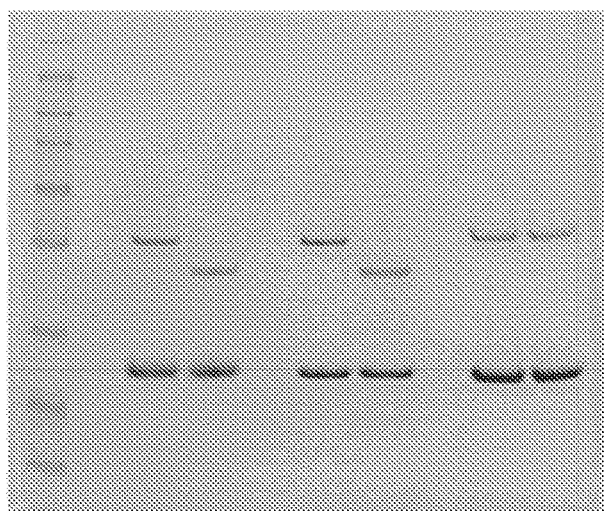
FIG. 9.
Figure 11:
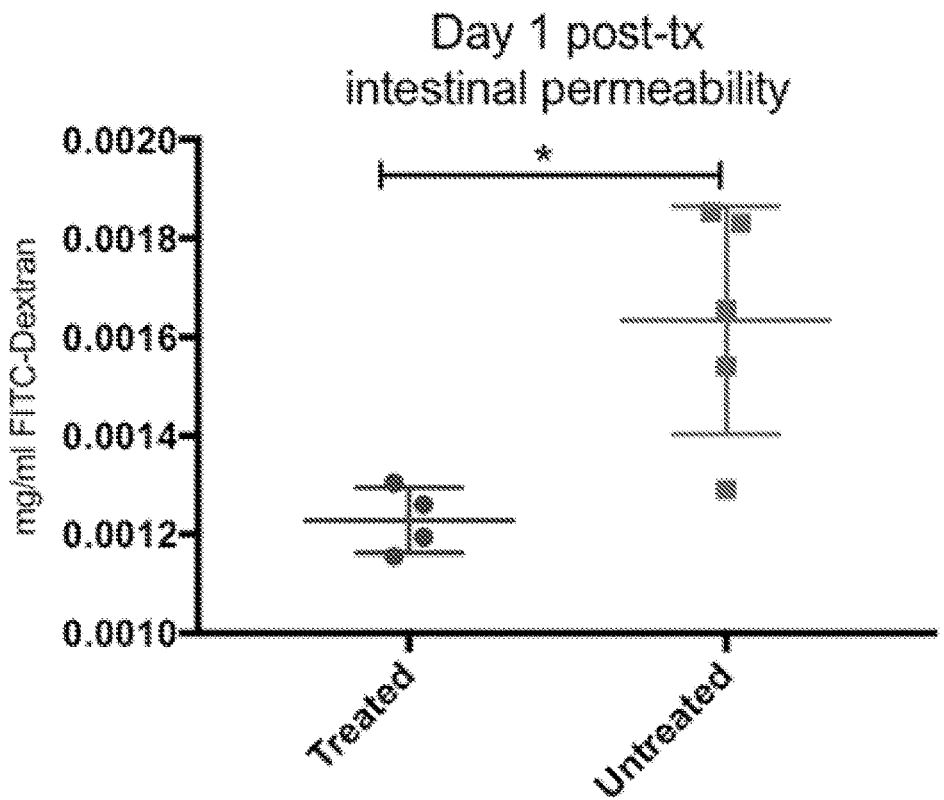
FIG. 11.

In veterinary applications, it is contemplated that the veterinarian will make the dosing decision based on the species, size, gender, age, physical condition, and weight of the animal, the duration of treatment, the nature of concurrent therapy, if any, the specific route of administration, and similar factors, in determining the amount of detoxified A subunit and carrier to administer. The formulations will typically be administered in the animal's drinking water. If the animal is free ranging, or has alternative water sources available and does not appear to like the taste of drinking water containing the therapeutic composition, the detoxified A subunit and carrier can be introduced into the animal by other methods used to administer veterinary drugs, such as by injection, by adding it as a food additive, or by administering the composition as a pill.

EXAMPLES

Example 1

This Example sets forth some methods and materials used in the studies discussed below.

Production of the E112K Mutant

E112K was prepared by galactose-affinity chromatography as described previously (Clements and. Finkelstein, Infect Immun. 1979, 24(3):760-9, Cheng et al., Vaccine, 2000, 18:38-49). Briefly, toxins were purified from *E. coli* expression cultures grown overnight in a 10-liter fermenter. Cells were harvested by centrifugation and lysed in a microfluidizer model M-110L (Miocrofluidics, Newton, MA). The cell lysates were dialyzed overnight in TEAN (0.05 M Tris, 0.001 M EDTA, 0.003 M $NaN_3$, 0.2 M NaCl, pH 7.5), clarified by centrifugation, and subjected to chromatography on separate immobilized D-galactose columns (Pierce, Rockford, IL). Toxins were eluted with 0.3 M galactose in TEAN and passed through an endotoxin removal column (Pierce, Rockford, IL). The composition and purity of each protein was confirmed by SDS-PAGE (FIG. 1 and FIG. 9) and Limulus Amebocyte Lysate assay (Lonza Inc, Walkersville, MD). The endotoxin content of the final products was <1 EU/mg. For final storage, 1 mg/ml solutions of protein were vialed in glass vials, frozen overnight, and then lyophilized.

Example 2

This Example shows that E112K prevents basal cytokine secretion and intracellular cAMP accumulation in intestinal cells.

As shown in FIGS. 2A-C, the E112K mutant is non-toxic, maintaining cell viability without inducing intestinal secretion. Confluent 6-well plates of epithelial cells or macrophages that were cultured with media alone or combined with E112K doses for 24 hours in 2 mls total volume. FIG. 2A presents Brightfield images of these culture wells. FIG. 2B shows viability staining results post-imaging by trypsinizing cells, washing, and staining for cytometric analyses in comparison with cells killed by heating to 95° C. for 3 mn. Data is shown as % dead cells. In a further study, BALB/c mice were administered E112K or LT by oral gavage. After 3 hours, the mice were euthanized and the gut/carcass weight ratios established. The results are shown in the graph presented as FIG. 2C. (Significance by one-way ANOVA analysis with Tukey's multiple comparison post-hoc test is shown as *$P \leq 0.05$, $P \leq 0.01$ and *$P \leq 0.001$ versus controls.)

It has been established for many years that LT induces cAMP accumulation through binding to host cell ARF to initiate ADP-ribosylation of Gsα, leading to irreversible activation of adenylate cyclase and increased production of intracellular cAMP (which ultimately leads to secretory diarrhea). E112K maintains the strong cellular binding and internalization properties of its parent molecule. Its A- and B-subunits can be detected inside human intestinal epithelial cells for up to seven days after in vitro treatment (FIG. 3A). In polarized epithelial cell monolayers, E112K lacks the ability to induce cAMP accumulation and subsequent ion secretion compared to the more toxic LT (FIGS. 3B, 3D). In the same culture system, our data indicates that while inflammatory IL-6 cytokine responses are slightly diminished, there is no major impact observed any observable changes on transwell epithelial monolayer integrity (FIGS. 3C, 3D). Similarly, in non-polarized monolayers of epithelial cells, E112K induces a 1000×-fold less cAMP production compared with 0.001 μg LT after 3 h treatments (in the presence of phosphodiesterases) and is consistent between protein lots of E112K even at 10 μg treatment or 10,000× excess protein compared with LT (FIG. 10). Intriguingly, pre-treatment of cells with E112K prevents LT-mediated cAMP accumulation (FIG. 3E). Thus, there is no evidence that E112K disrupts normal intestinal function beyond acting as an anti-inflammatory agent. These results further demonstrate a surprising property of E112K in prevention of intracellular signaling. Without wishing to be bound by theory, we surmise that E112K sequesters host cell ARF, which then limits molecular signaling pathways resulting in decrease cytokine production and intracellular cAMP accumulation upon external cellular stimulation (FIG. 11).

Example 3

This Example shows that E112K inhibits intracellular cAMP, ADP-ribosylation, and activation of dendritic cells.

One of the consequences of LT intoxication of cells is ADP-ribosylation of host cell proteins and accumulation of cAMP. in dendritic cells, this leads to activation and upregulation of costimulatory surface markers, such as CD80 and CD86. Dendritic cells are key initiators of adaptive immune responses, linking the traditional innate and adaptive arms of the immune system. E112K is rapidly internalized and its A- and B-subunits detected in treated dendritic cells (FIG. 4A).

Unlike LT, E112K will prevent cAMP accumulation in stimulated dendritic cells (FIG. 4B). Furthermore, pretreatment of dendritic cells with E112K inhibits intracellular ADP-ribosylation of host cell proteins by LT and LT-mediated activation (FIGS. 4B, 4C). Pre-treatment of dendritic cells with E112K, prior to LPS-stimulation also results in decreased dendritic cell activation. These changes are not seen with LTB treatment, which once again strongly indicates a key role for E112K's inactivated A-subunit in its immunosuppressive properties. These results confirm the surprising property of E112K in preventing intracellular signaling and cellular activation.

Example 4

This Example shows that E112K inhibits adaptive immunity.

For decades, LT has been known as a potent mucosal and parenteral adjuvant, inducing immune responses to admixed antigens. Older studies also clearly determined that E112K and related mutants with mutations in the A-subunit (e.g., E110D, S61F) that prevent ADP-ribosylation activity are not oral adjuvants (Lobet et al, Infect Immun. 1991, 59(9):2870-9, Cheng et al., Vaccine, 2000, 18:38-49). Similarly, in our studies, increasing doses of E112K admixed with tetanus toxoid result in a progressive decline in antigen-specific antibody responses (FIG. 5). While isolated B-subunit (LTB) is also not a good adjuvant, it does not lead to the progressive decrease in adaptive immunity seen with E112K. Thus, unlike other members of the LT protein family, E112K acts uniquely on the immune system and can inhibit antigen-specific responses to highly immunogenic antigens. This may be an ideal property during autoimmune inflammatory diseases, such as antigen specific responses to specific commensal bacterial that have been reported for Crohn's disease and ulcerative colitis.

Example 5

This Example shows that E112K improves inflammatory bowel disease pathologies in dextran sulphate sodium (DSS) colitis mouse models. The classic DSS chemical injury model of chronic, ulcerative colitis was induced in BALB/c mice by successive waves of 5-day drinking water treatment with 4% DSS, followed by 7-days of water. After the 2nd (day 17) or 3rd (day 29) DSS treatment, some mice were treated with 50 μg E112K by oral gavage. The final weight change (day 36, % original weight) or colon length (day 38, mm) were evaluated for all groups. The results are presented in FIG. 6A. FIG. 6B presents H&E pictures of swiss-rolled, processed colonic mouse intestines (from day 38 collected samples). The intestines show some moderation of DSS-mediated cellular infiltration (black asterisk) with E112K therapy.

Example 6

This Example shows that E112K is a safe, efficacious therapy for inflammatory bowel disease pathology in the IL-10−/− colitis mouse model.

FIG. 7A shows that the weight gain over time after 200 μg E112K by oral gavage in IL-10−/− female and male mice is similar to that of naïve (control) mice. The chronic colitis model was induced in IL-10−/− mice with 7 day exposure to 200 ppm piroxicam at 6-weeks of age. Piroxicam diet (in food gel, formulated food, or powder food) induces colitis pathology at week 10. Colon histology scores were tallied using composite scoring of 4 colonic sections for type and extent of mucosal and inflammatory changes by a pathologist blinded to the animal treatments. As shown in FIG. 7B, 200 μg E112K by oral gavage ("O") did not induce any intestinal pathology. FIG. 7C presents examples of H&E-stained colons from piroxicam-treated animals exhibiting typical pathology, including hyperplasia (top photo, asterisk) and ulceration of intestinal wall (bottom photo, asterisk). The chronic colitis model was induced in IL-10−/− mice with 7 day exposure to 200 ppm piroxicam at 6-weeks of age. FIG. 7D presents the colon histology score of control mice and of mice subjected to piroxicam exposure followed after that exposure by weekly E112K treatment by either intraperitoneal ("IP") injection or oral gavage ("O") for three weeks. In a separate experiment, groups of mice (n=5-6) were exposed to piroxicam and then either untreated or given 100 μg E112K by oral gavage weekly for three weeks. On week 10, mice were fed 4 kD FITC-Dextran at 60 mg/1.00 g body weight by oral gavage 3 h prior to euthanasia. Serum was collected and then analyzed for levels of fluorescent protein after 3 h oral gavage with at week 10. The results are shown in FIG. 7E. Significance is shown as $^{*}P \leq 0.05$, $^{}P \leq 0.01$ and $^{*}P \leq 0.001$.

Example 7

This Example discusses and extends the studies reported in Example 6.

As indicated in FIG. 6, oral E112K ameliorates symptoms of a chemically induced model of inflammatory bowel disease (via. DSS), including weight loss, colon shortening and epithelial cell hyperplasia and mucosal inflammation. In the IL-10−/− model of chronic colitis, up to 200 μg oral E112K therapy alone does not impact weight loss or development of IBD pathology (FIGS. 7A, 7B).

However, in piroxicam-treated mice that have observable histopathology, including architectural distortion like hyperplasia of the intestinal mucosa, inflammation, and ulceration (FIG. 7C, asterisks), weekly treatment with 100 μg E112K for three weeks by oral gavage improved histology scores and reduced intestinal permeability (FIGS. 7D, 7E). These changes were similar to 10 μg E112K orally but greater than just 1 or 10 μg of E112K parenterally in reducing intestinal pathology (FIG. 7D).

Finally, we tested E112K for efficacy in a third model of inflammatory bowel disease, the T-cell transfer model of colitis. In this model, CD4+CD45RB-hi T-cells are transferred into Rag1−/− mice, causing unchecked intestinal inflammation and wasting (or weight loss) by 20 weeks. The protocol is presented graphically in FIG. 8A. Mice that received 100 μg. E112K by oral gavage on weeks 13, 16, and 18 ("O E112K") exhibited improved pathology scores (FIG. 8B), showed no abnormal weight loss (FIG. 8C), and showed normal stool consistency (FIG. 8D).

Thus, E112K was shown to be an effective therapy for IBD in three different mouse models of colitis.

Example 8

This Example shows that the exemplar detoxified A subunit-carrier E112K improved intestinal permeability as soon as 24 hours post-treatment. The chronic colitis model was induced in IL-10−/− mice with 7 day exposure to 200 ppm piroxicam at 6-weeks of age. IL-10−/− mice were exposed to piroxicam for 7 days in rodent chow and then 4 days later either left untreated or treated with E112K in drinking water. Intestinal permeability was tested 1-day after treatment by analyzing serum for fluorescent protein after 3 h oral gavage with 4 kD FITC-Dextran. The results are shown in FIG. 11. Significance is shown as *P≤0.05.

Example 9

Figure 12:
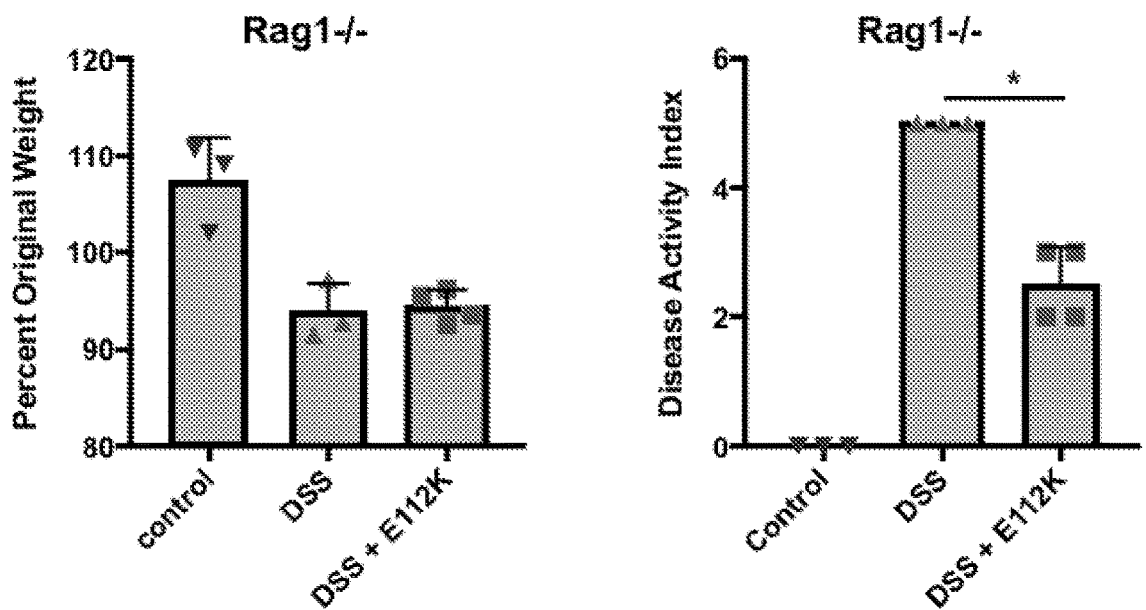
FIG. 12.
Figure 14:
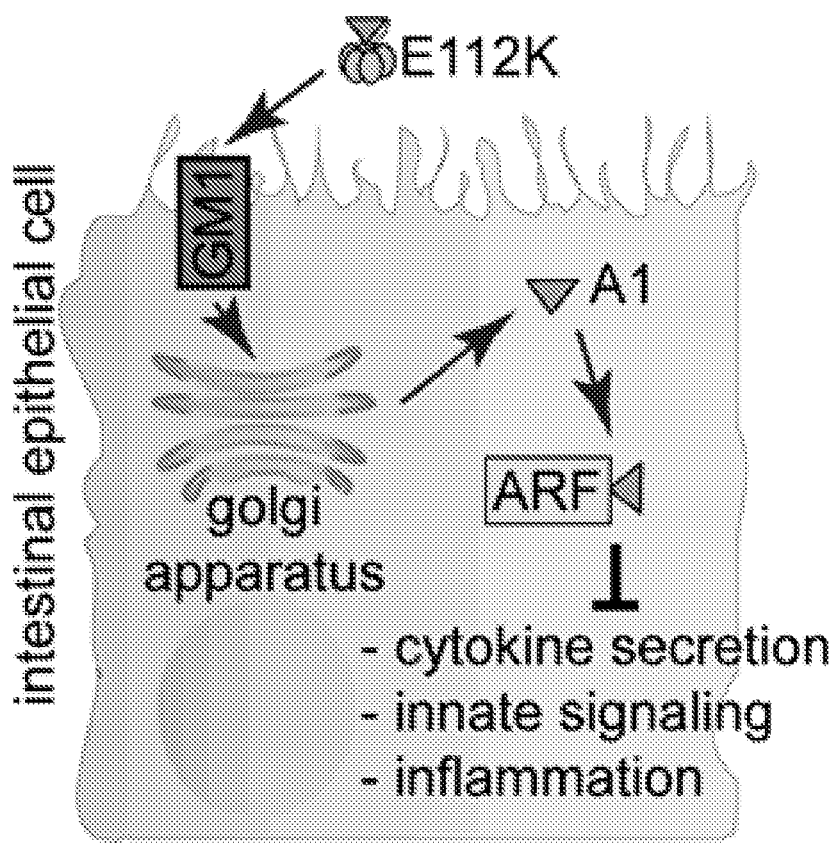
FIG. 14.

This Example shows that the exemplar detoxified A subunit-carrier E112K improved disease activity index in DSS acute model of colitis in immunodeficient mice. Rag1−/− mice that lack functional adaptive immune system were exposed to 3% DSS in drinking water for 7 days. A group of these DSS mice were treated with oral E112K on day 5. Weight changes and disease activity index (evaluated by weight loss, fecal consistency, and blood in feces) were evaluated in animals at day 8. The results are shown in graph form in FIG. 12. As shown in FIG. 12, E112K treatment improved the disease activity index, but not weight loss, indicating that at least some of E112K immunomodulatory effects are T-cell independent.

Example 10

$1\times10^6$ bone-marrow derived mouse dendritic cells were treated in triplicate for 48 h with 0.1 µg/ml test proteins before analysis of CD80 and CD86 co-stimulatory marker levels on CD11c+ gated cells. Assay was performed three independent times. FIG. 13A presents representative dot blots and mean fluorescent intensity levels (MFI) from one experiment. Th2-promoting cytokines and Th1/Th17-promoting cytokines were assayed from culture supernatants of $1\times10^6$ CD11c+ purified DC cultured with 0.1 µg/ml test proteins in triplicate for 5 days. As shown in FIGS. 13B and C, ETEC LT B subunit ("LTB") partially activated dendritic cells, similar to holotoxin ("LT") and mutated $AB_5$ proteins that act as adjuvants, mLT (LT-R192G), and dmLT (LT-R192G/L211A), including increased expression of co-stimulatory marker CD86 and secretion of IL-12p70, RANTES, and IL-6 cytokines, while E112K did not induce the expression or secretion of these or other cytokines. The expression of IL-6 induced by E112K, for example, was similar to that of the control group, while high levels of IL-6 were induced by LT, LTB, and the two mutated holotoxins. Similar cytokine profiles can be seen for the other Th1-promoting cytokines assayed and for the other Th17-promoting cytokines assayed.

Example 11

This Example discusses a possible mechanism of action for detoxified LT mutants such as E112K.

Without wishing to be bound by theory, it is believed that the intact detoxified LT mutant E112K binds to GM1 surface receptors on cells such as epithelial cells through B-subunit binding. It is further believed that the binding results in release of the E112K A1-subunit into the cytosol, that it is the A1-subunit that interferes with function of ADP-ribosylation factor (ARF) in the host cell, and that it is the interference of the A1-subunit with ARF activity that inhibits ongoing vesicular trafficking and innate signaling (e.g., IL-6 cytokine secretion) and decreases cAMP levels over time, ultimately dampening overall levels of inflammation. Thus, it is believed that the A1-subunit interference with ARF activity suppresses the release of inflammatory cytokines, suppresses pro-inflammatory signaling responses, and suppresses inflammation, as shown in cartoon form in FIG. 13. Since it is believed that the role of the B-subunit is to act as a carrier to carry the A1-subunit into the cell and allow it to translocate from the Golgi apparatus to the cytosol, it is believed that other carriers enabling cellular targeting, cellular entry, or both, can be used as carriers of the A1-subunit and act to reduce inflammation in subjects to which such carrier-detoxified LT A1-subunits are administered.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method of reducing symptoms of inflammation in a subject in need thereof, said method comprising administering by an oral route, a topical route, a rectal route, an intravenous route, a transdermal route, an intramuscular route, an endoscopic route, or a parenteral route to said subject a composition comprising a therapeutically effective amount of: (a) (i) an *E. coli* heat labile enterotoxin ("LT") non-toxic A subunit which does not have activity as an adjuvant, (ii) a LT non-toxic A1 subunit which does not have activity as an adjuvant, or, (iii) a combination of said non-toxic A subunit and said non-toxic A1 subunit, and, (b) a carrier which causes internalization of said non-toxic A subunit or non-toxic A1 subunit, or combination thereof, into cells, wherein said inflammation is inflammatory bowel disease, optionally wherein said inflammatory bowel disease is ulcerative colitis or Crohn's disease, and wherein said non-toxic A subunit, non-toxic A1 subunit, or combination thereof has a substitution mutation in said A subunit, said A1 subunit, or both, in an amino acid residue selected from the group consisting of E112, E110, and R25, said mutation consisting of: E112D, E112K, E112R, E112G, E112A, E112V, E112L, E112I, E112M, E112S, E112T, E112N, E110K, E110R, E110G, E110A, E110V, E110L, E110I, E110M, E110S, E110T, E112N, R25G, R25D, R25E, R25A, R25V, R25L, R25I , R25M, R25S, or R25T.

2. The method of claim 1, further wherein said non-toxic A subunit or said non-toxic A1 subunit, or said combination of said non-toxic A subunit and said non-toxic A1 subunit does not induce intracellular cAMP accumulation in an epithelial cell.

3. The method of claim 1, further wherein said non-toxic A subunit or said non-toxic A1 subunit, or said combination of said non-toxic A subunit and said non-toxic A1 subunit does not activate expression and secretion of IL-6 in murine dendritic cells when said cells are contacted in vitro with said non-toxic A subunit or said non-toxic A1 subunit, or said combination of said non-toxic A subunit and said non-toxic A1 subunit in a medium that supports growth of said murine dendritic cells, compared to expression and secretion of IL-6 by said cells in said medium when said cells are contacted in vitro with LT B subunit.

4. The method of claim 1, wherein said carrier which causes internalization of said non-toxic A subunit, non-toxic A1 subunit, or combination thereof, into cells is a LT B subunit or a cholera toxin B subunit ("CTB") or cholera A2 domain and B subunit ("CTA2/B"), optionally wherein said non-toxic A subunit, non-toxic A1 subunit, or combination thereof is chemically conjugated or recombinantly fused to said LT B subunit or to said CTB or said CTA2/B subunit, respectively.

5. The method of claim 1, wherein said carrier which causes internalization of said non-toxic A subunit, non-toxic A1 subunit, or combination thereof, into cells is a liposome or encapsulated vesicle.

6. The method of claim 5, wherein said carrier is a liposome and said liposome is targeted to a cell antigen by an antibody or antigen-binding fragment or derivative thereof which maintains antigen-binding.

7. The method of claim 1, wherein said carrier which causes internalization of said non-toxic A subunit, non-toxic A1 subunit, or combination thereof, into cells is a β-glucan.

8. The method of claim 1, wherein said mutation in said amino acid residue of said A subunit, said A1 subunit, or both, is selected from the group consisting of E112K, E112G, E112D, E112R, E110K, E110G, and R25G.

9. The method of claim 1, wherein said therapeutically effective amount is administered as an induction dose followed by one or more maintenance doses.

10. The method of claim 1, wherein said therapeutically effective amount of said composition is from 500 μg to 500 mg.

11. The method of claim 8, wherein said mutation in said A subunit, said A1 subunit, or both, is E112K, E112G, or E112R.

12. The method of claim 8, wherein said mutation in said A subunit, said A1 subunit, or both, is E112K.

13. The method of claim 8, wherein said mutation in said A subunit, said A1 subunit, or both, is E112K, E112R, or E112G.

14. The method of claim 8, wherein said mutation in said A subunit, said A1 subunit, or both, is E112K or E112R.

15. The method of claim 8, wherein said mutation in said A subunit, said A1 subunit, or both, is R25G, R25E, or R25D.

16. The method of claim 8, wherein said administering is by an oral route, a topical route, a rectal route, an intravenous route, a transdermal route, an intramuscular route, or a parenteral route.

17. The method of claim 1, wherein said mutation in said amino acid residue of said A subunit, said A1 subunit, or both, is selected from the group consisting of E112A, E112V, E112L, and E112I.

18. The method of claim 1, wherein said mutation in said amino acid residue of said A subunit, said A1 subunit, or both, is selected from the group consisting of E110A, E110V, E110L, and E110I.

19. The method of claim 1, wherein said mutation in said amino acid residue of said A subunit, said A1 subunit, or both, is selected from the group consisting of R25A, R25V, R25L, and R25I.

* * * * *